US012575623B2

(12) United States Patent
Skalos et al.

(10) Patent No.: US 12,575,623 B2
(45) Date of Patent: Mar. 17, 2026

(54) FEATURES FOR SUPPORT GARMENT FOR A WEARABLE MEDICAL DEVICE

(71) Applicant: ZOLL Medical Corporation, Chelmsford, MA (US)

(72) Inventors: Philip C. Skalos, Pittsburgh, PA (US); Christopher Lawrence Swenglish, Connellsville, PA (US); Sunaina Rustagi, Presto, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 716 days.

(21) Appl. No.: 17/494,105

(22) Filed: Oct. 5, 2021

(65) Prior Publication Data

US 2022/0104566 A1 Apr. 7, 2022

Related U.S. Application Data

(60) Provisional application No. 63/088,211, filed on Oct. 6, 2020.

(51) Int. Cl.
A61N 1/39 (2006.01)
A41D 13/12 (2006.01)

(52) U.S. Cl.
CPC ....... A41D 13/1281 (2013.01); A61N 1/3904 (2017.08)

(58) Field of Classification Search
CPC .... A61N 1/3904; A61N 1/0484; A61N 1/046; A61D 13/1281
See application file for complete search history.

(56) References Cited

U.S. PATENT DOCUMENTS

| | | | |
|---|---|---|---|
| 4,928,690 A | 5/1990 | Heilman et al. | |
| 5,078,134 A | 1/1992 | Heilman et al. | |
| 5,741,306 A | 4/1998 | Glegyak et al. | |
| 5,944,669 A | 8/1999 | Kaib | |
| 6,065,154 A | 5/2000 | Hulings et al. | |
| 6,253,099 B1 | 6/2001 | Oskin et al. | |
| 6,280,461 B1 | 8/2001 | Glegyak et al. | |
| 6,681,003 B2 | 1/2004 | Linder et al. | |
| 6,941,775 B2 | 9/2005 | Sharma | |

(Continued)

FOREIGN PATENT DOCUMENTS

| | | |
|---|---|---|
| CN | 106646502 A | 5/2017 |
| CN | 206460170 U | 9/2017 |

(Continued)

*Primary Examiner* — Joseph M Dietrich
(74) *Attorney, Agent, or Firm* — ZOLL Medical Corporation

(57) ABSTRACT

A wearable cardiac therapeutic device includes a plurality of ECG sensing electrodes configured to sense ECG signals regarding a cardiac function of a patient; a plurality of therapy electrodes configured to deliver transcutaneous defibrillation shocks or transcutaneous pacing pulses to the patient's heart; and a support garment configured to support and hold the plurality of ECG sensing electrodes and the plurality of therapy electrodes against the patient's body. The support garment includes one or more features for improving and enhancing the patient's experience in wearing the support garment with respect to wearability, comfort, aesthetics, and assembly and usage of the device.

20 Claims, 23 Drawing Sheets

(56)                References Cited

U.S. PATENT DOCUMENTS

| 8,271,082 | B2 | 9/2012 | Donnelly et al. | |
| 8,369,944 | B2 | 2/2013 | Macho et al. | |
| D779,738 | S | 2/2017 | Chow et al. | |
| 9,782,104 | B2 | 10/2017 | MacEachern et al. | |
| 9,782,578 | B2 | 10/2017 | Kaib et al. | |
| 10,535,278 | B2 | 1/2020 | Chahine | |
| 2010/0068971 | A1* | 3/2010 | Hendrickson | A41C 3/04 |
| | | | | 2/104 |
| 2016/0076176 | A1 | 3/2016 | Rock et al. | |
| 2017/0036066 | A1 | 2/2017 | Chahine | |
| 2017/0056644 | A1 | 3/2017 | Chahine et al. | |
| 2017/0079348 | A1 | 3/2017 | Chahine et al. | |
| 2018/0243549 | A1* | 8/2018 | Hill | A41C 3/0007 |
| 2018/0345015 | A1 | 12/2018 | Straka et al. | |
| 2019/0000384 | A1 | 1/2019 | Gupta et al. | |
| 2019/0112736 | A1 | 4/2019 | Rock et al. | |
| 2019/0298987 | A1* | 10/2019 | Freeman | A61B 5/282 |
| 2019/0352814 | A1 | 11/2019 | Rock et al. | |
| 2020/0069250 | A1 | 3/2020 | Chahine et al. | |
| 2020/0107731 | A1 | 4/2020 | Straka et al. | |
| 2020/0144777 | A1 | 5/2020 | Chahine et al. | |
| 2020/0314184 | A1 | 10/2020 | Etemad et al. | |
| 2020/0367823 | A1 | 11/2020 | Chahine et al. | |

FOREIGN PATENT DOCUMENTS

| CN | 206920606 | U | 1/2018 |
| CN | 111343901 | A | 6/2020 |
| EP | 3646339 | A1 | 1/2019 |
| EP | 3665690 | A1 | 1/2019 |
| WO | 2016149829 | A1 | 9/2016 |
| WO | 2019000073 | A1 | 1/2019 |
| WO | 2019006536 | A1 | 1/2019 |
| WO | 2019134031 | A2 | 7/2019 |
| WO | 2019134032 | A1 | 7/2019 |
| WO | 2019134033 | A2 | 7/2019 |
| WO | 2019222845 | A1 | 11/2019 |
| WO | 2019222846 | A1 | 11/2019 |
| WO | 2020099905 | A1 | 5/2020 |
| WO | 2020099906 | A1 | 5/2020 |
| WO | 2020099907 | A1 | 5/2020 |
| WO | 2020142838 | A1 | 7/2020 |
| WO | 2020142843 | A1 | 7/2020 |

* cited by examiner

FIG. 9A                    FIG. 9B

FEATURES FOR SUPPORT GARMENT FOR A WEARABLE MEDICAL DEVICE

CROSS REFERENCE TO RELATED APPLICATIONS

This application claims the benefit of U.S. Provisional Patent Application No. 63/088,211 filed Oct. 6, 2020, entitled "Features for Support Garment for a Wearable Medical Device", the disclosure of which is hereby incorporated in its entirety by reference.

FIELD OF THE DISCLOSURE

The present disclosure relates to a support garment for a wearable cardiac monitoring and therapeutic medical device, such as a wearable cardioverter defibrillator (WCD).

BACKGROUND OF THE DISCLOSURE

One of the most deadly forms of heart arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Although frequently not noticeable to the victim, ventricular fibrillation is often preceded by ventricular tachycardia, which is a regular but fast rhythm of the heart. Because the victim has no noticeable warning of the impending fibrillation, death often occurs before the necessary medical assistance can arrive.

Because time delays in applying the corrective electrical treatment can result in death, pacemakers and defibrillators have significantly improved the ability to treat these otherwise life-threatening conditions. Normal heart function often can be restored to a person suffering ventricular fibrillation or ventricular tachycardia by a procedure known as cardioversion, the synchronized application of electrical therapy to the heart muscle. Pacemakers and defibrillators that apply corrective electrical pulses externally to the patient's chest wall also are used to correct such life-threatening arrhythmias, but suffer from a drawback insofar as it cannot be possible to apply the device in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. However, patients who have recently had a heart attack or are awaiting such an implantable device can be kept in a hospital where corrective electrical therapy is generally close at hand. Long-term hospitalization is frequently impractical due to its high cost, or due to the need for patients to engage in normal daily activities.

Wearable defibrillators have been developed for patients who have recently experienced cardiac arrest, who are susceptible to heart arrhythmias and are at temporary risk of sudden death, and who are awaiting an implantable device. Support garments have been developed for housing the components of such wearable defibrillators, particularly the sensing and therapeutic energy delivery electrodes, such that the electrodes are properly positioned against the patient's skin. The patient may be required to wear the support garment and the components continuously or nearly continuously for extensive periods of time. Over these extensive periods of time, the patient may experience discomfort while wearing the support garment, frustration or embarrassment with the appearance or cleanliness of the support garment, difficulties with assembling the components on the support garment, and difficulties fastening the support garment on the body. Patients may benefit from a wearable cardioverter defibrillator garment that includes features for enhancing the patient's experience in wearing the support garment with respect to wearability, comfort, aesthetics, and ease of assembly and usage of the device.

SUMMARY OF SOME OF THE EMBODIMENTS

The support garments of the present disclosure can comprise or consist of one or more of, or any combination of, the feature(s) described herein or feature(s) of the examples described herein. Non-limiting examples of embodiments will now be described.

In an example, a cardiac therapeutic device support garment for easy and quick electrode assembly thereupon is provided. The device can comprise: a plurality of ECG sensing electrodes configured to sense ECG signals regarding a cardiac function of a patient; and the support garment configured to support and hold the plurality of ECG sensing electrodes against a patient's body. The support garment can comprise a plurality of fasteners on an inside surface thereof for fastening and supporting the plurality of ECG sensing electrodes on the support garment. Each of the plurality of fasteners can comprise a circular hook-and-loop fastener patch permanently affixed to a predetermined location on the inside surface of the support garment. Each of the plurality of ECG sensing electrodes can comprise a corresponding hook-and-loop fastener configured to connect to a respective circular hook-and-loop fastener patch on the support garment. The circular hook-and-loop fastener patches are configured to facilitate alignment and assembly of the respective ECG sensing electrodes on the support garment and provide for fastening and support for the respective ECG sensing electrodes on the support garment independent of the rotational orientation of the respective ECG sensing electrodes.

Each of the circular hook-and-loop fastener patches can have a diameter of approximately 0.5"-3.0".

Each of the circular hook-and-loop fastener patches can have a diameter of approximately 1.25".

The circular hook-and-loop fastener patches can comprise a nylon, polyester, or polypropylene material.

The circular hook-and-loop fastener patches and the corresponding hook-and-loop fasteners can be color coded to facilitate assembly of each of the plurality of ECG sensing electrodes to a corresponding predetermined location on the inside surface of the support garment.

The device can further comprise a plurality of therapy electrodes configured to deliver transcutaneous defibrillation shocks or transcutaneous pacing pulses to the patient's heart, the support garment being configured to support and hold the plurality of therapy electrodes against the patient's body.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller can be configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a cardiac therapeutic device support garment for easy and quick therapy electrode assembly thereupon is provided. The device can comprise: a plurality of therapy electrodes configured to deliver transcutaneous defibrillation shocks or transcutaneous pacing pulses to a patient's heart; and the support garment configured to support and hold the plurality of therapy electrodes against the patient's body. The support garment can comprise: a plurality of support pockets disposed on an inside surface of the support garment for supporting the plurality of therapy electrodes on the support garment; and a plurality of handling tab members, at least one handling tab member being fastened to each of the plurality of support pockets, the handling tab members being configured to facilitate opening and closing of the plurality of support pockets for assembly of the plurality of therapy electrodes therein. Each of the handling tab members can comprise a fabric tape formed in a loop extending from an outer surface of a respective one of the plurality of support pockets to an inner surface of the respective support pocket. Each of the handling tab members can have a length and width configured to facilitate physical manipulation of the handling tab member by grasping the handling tab member and/or inserting a finger into the loop.

The fabric tape of each of the handling tab members can have a width of approximately 0.5"-1.5", more particularly approximately 1.0" and a length of approximately 5"-10", more particularly approximately 6"-8", more particularly approximately 6.5".

The fabric tape of each of the handling tab members can comprise a cotton twill material.

Each of the handling tab members can be color coded to correspond to a colored indicator provided on a respective therapy electrode.

Each of the handling tab members can be fastened to an open end of the respective support pocket and/or to an at least partially open side of the respective support pocket.

Each of the handling tab members can comprise a female or male plastic snap member disposed thereon configured to form a mating engagement with a counterpart male or female plastic snap member disposed on the inside surface of the support garment for releasably securing the respective support pocket in a closed condition.

The device can further comprise a plurality of ECG sensing electrodes configured to sense ECG signals regarding a cardiac function of the patient, the support garment being configured to support and hold the plurality of ECG sensing electrodes against the patient's body.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a cardiac therapeutic support garment for promoting aesthetic appeal thereof is provided. The device can comprise: a plurality of ECG sensing electrodes configured to sense ECG signals regarding a cardiac function of a patient; a plurality of therapy electrodes configured to deliver transcutaneous defibrillation shocks or transcutaneous pacing pulses to the patient's heart; and the support garment configured to support and hold the plurality of ECG sensing electrodes and the plurality of therapy electrodes against the patient's body. The support garment can comprise a back portion; and a belt defined by side portions extending from the back portion and around a front of the patient's torso. The back portion and the side portions defining the belt can be secured by a seam formed by aesthetic flatlock stitching.

The flatlock stitching can conform to ISO 607.

The flatlock stitching can comprise approximately 10-20 stitches per inch, more particularly approximately 12-16 stitches per inch, more particularly approximately 14 stitches per inch.

The flatlock stitching can comprise a textured polyester thread having a size of approximately 18-30 tex, more particularly approximately 22-28 tex, more particularly approximately 24 tex, and a strength of approximately 1 lb.-3 lbs., more particularly approximately 1.5 lbs.-2.5 lbs, more particularly 2.02 lbs.

The flatlock stitching can comprise a polyester wrapped, polyester core thread having a size of approximately 18-30 tex, more particularly 22-28 tex, and more particularly 24 tex, and a strength of approximately 1.5 lbs.-3.5 lbs., more particularly approximately 2.0 lb.-3.0 lb., and more particularly 2.77 lb.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a cardiac therapeutic device support garment for easy assembly, donning, and removal thereof by physically infirm patients is provided. The device can comprise: a plurality of therapy electrodes configured to deliver transcutaneous defibrillation shocks or transcutaneous pacing pulses to a patient's heart; a distribution box; and the support garment configured to support plurality of therapy electrodes and the distribution box and hold the plurality of therapy electrodes against the patient's body. The support garment can comprise: a plurality of support members disposed on an inside surface of the support garment for supporting the plurality of therapy electrodes and the distribution box on the support garment; and a plurality of plastic snaps for fastening the plurality of support members on the support garment to secure the distribution box and the plurality of therapy electrodes on the support garment, at least one plastic snap being provided to fasten each of the plurality of support members. Each of the plurality of plastic snaps is configured to facilitate physical manipulation and fastening or unfastening of a respective support member and provide tactile feedback when the plastic snaps are secured.

The plurality of support members can comprise at least one support pocket for securing at least one of the plurality of therapy electrodes on the support garment and at least one of the plurality of plastic snaps is disposed on the at least one support pocket and the inside surface of the support garment for releasably securing the at least one support pocket in a closed condition. The plurality of support members can further comprise at least one flap for securing the distribution box on the support garment and at least one of the plastic snaps is disposed on the at least one flap and the inside surface the support garment for releasably securing the flap in a position securing the distribution box. Each of the plurality of plastic snaps can comprise a male or female plastic snap member disposed on the respective support member and a counterpart female or male plastic snap member disposed on the inside surface of the support garment. An arrangement of the male and female plastic snap members of the at least one plastic snap for releasably securing the at least one support pocket can be reversed from an arrangement of the male and female plastic snap members for releasably securing the at least one flap.

The male and female plastic snap members of each of the plurality of plastic snaps can be secured to the respective support member and the inside surface support garment by a color coded fabric tape indicating the counterpart male and female plastic snap members and the at least one of the plurality of therapy electrodes or the distribution box being secured by the respective support member.

Each of the plurality of plastic snaps can have a maximum diameter of approximately 10 mm-20 mm, more particularly approximately 14-16 mm, more particularly approximately 14.5 mm-15.5 mm, more particularly 14.7 mm.

Each of the plurality of plastic snaps can have a medium standard snap force. A force required to fasten and/or unfasten each of the plurality of plastic snaps can be approximately
1 lbf-4 lbf, more particularly 1.5 lbf-3 lbf, and more particularly 1.75 lbf-2.5 lbf.

The device can further comprise a plurality of ECG sensing electrodes configured to sense ECG signals regarding a cardiac function of a patient, the support garment being configured to support and hold the plurality of ECG sensing electrodes against the patient's body.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a cardiac therapeutic device support garment for promoting aesthetic appeal thereof is provided. The device can comprise: a plurality of ECG sensing electrodes configured to sense ECG signals regarding a cardiac function of a patient; a plurality of therapy electrodes configured to deliver transcutaneous defibrillation shocks or transcutaneous pacing pulses to the patient's heart; and a support garment configured to support and hold the plurality of ECG sensing electrodes and the plurality of therapy electrodes against the patient's body. The support garment can comprise a gray color fabric material.

The gray color fabric material comprises PANTONE 16-3850 TPX.

The gray color fabric material can have an anti-microbial treatment applied thereto.

The anti-microbial treatment can comprise a polymer application configured to deliver silver ions.

The gray color fabric material can comprise a tricot fabric. The tricot fabric can comprise nylon and spandex materials. The tricot fabric can comprise approximately 65%-90% nylon material, more particularly 70%-85% nylon material, more particularly 77% nylon material.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a cardiac therapeutic device support garment for promoting hygienic long term and/or continuous use thereof is provided. The device can comprise a plurality of ECG sensing electrodes configured to sense ECG signals regarding a cardiac function of a patient; a plurality of therapy electrodes configured to deliver transcutaneous defibrillation shocks or transcutaneous pacing pulses to the patient's heart; and the support garment configured to support and hold the plurality of ECG sensing electrodes and the plurality of therapy electrodes against the patient's body. The support garment can comprise a fabric having an anti-microbial treatment applied thereto. The anti-microbial treatment is configured to limit or prevent odor and bacterial growth on the support garment.

The anti-microbial treatment can comprise a polymer application configured to deliver silver ions.

The fabric can have a gray color.

The fabric can comprise a tricot fabric. The tricot fabric can comprise nylon and spandex materials. The tricot fabric can comprise approximately 65%-90% nylon material, more particularly 70%-85% nylon material, more particularly 77% nylon material.

The fabric of the support garment can be configured to wick moisture from the patient's skin.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a cardiac therapeutic device support garment for promoting comfort and aesthetic appeal thereof is provided. The device can comprise: a plurality of ECG sensing electrodes configured to sense ECG signals regarding a cardiac function of a patient; a plurality of therapy electrodes configured to deliver transcutaneous defibrillation shocks or transcutaneous pacing pulses to the patient's heart; and the support garment configured to support and hold the plurality of ECG sensing electrodes and the plurality of therapy electrodes against the patient's body. The support garment can comprise an aesthetic edge binding surrounding at least a portion of a periphery of the support garment, the aesthetic edge binding comprising nylon and spandex materials.

The edge binding can be formed in a V-fold configuration.

The edge binding can have a width of approximately 12 mm-20 mm, more particularly approximately 14 mm-18 mm, more particularly approximately 15 mm-17 mm, more particularly approximately 16 mm. The edge binding can have a thickness of approximately 0.4 mm-1.2 mm, more particularly approximately 0.6 mm-1.0 mm, more particularly approximately 0.75 mm-0.85 mm, more particularly approximately 0.8 mm.

The edge binding can comprise approximately 85%-95% nylon material, more particularly approximately 88%-94% nylon material, more particularly approximately 91% nylon material.

The edge binding can have a color complementary to a color of a fabric of the support garment.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a cardiac therapeutic device support garment for promoting comfort during long term and/or continuous wear thereof is provided. The device can comprise: a plurality of ECG sensing electrodes configured to sense ECG signals regarding a cardiac function of a patient; a plurality of therapy electrodes configured to deliver transcutaneous defibrillation shocks or transcutaneous pacing pulses to the patient's heart; and the support garment configured to support and hold the plurality of ECG sensing electrodes and the plurality of therapy electrodes against the patient's body. The support garment can comprise: a back portion; a belt defined by side portions extending from the back portion and around a front of the patient's torso; and at least one shoulder strap extending between the back portion and the belt, the at least one shoulder strap comprising a double plush elastic material.

The at least one shoulder strap can have a width of approximately 0.5"-1.5", more particularly approximately 0.75"-1.25", more particularly approximately 0.9"-1.1", more particularly approximately 1.0".

The double plush elastic material of the at least one shoulder strap can comprise polyester, spandex, and nylon materials.

The double plush elastic material of the at least one shoulder strap can have a color complementary to a color of a fabric of the support garment.

The double plush elastic material of the at least one should strap can have an elastic elongation of 125%-200%, more particularly 140%-160%, more particularly 150%.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a cardiac therapeutic device support garment for easy and quick donning and removal about the torso of the patient is provided. The device can comprise: a plurality of ECG sensing electrodes configured to sense ECG signals regarding a cardiac function of a patient; a plurality of therapy electrodes configured to deliver transcutaneous defibrillation shocks or transcutaneous pacing pulses to the patient's heart; and the support garment configured to support and hold the plurality of ECG sensing electrodes and the plurality of therapy electrodes against the patient's body. The support garment can comprise: a back portion; a belt defined by side portions extending from the back portion and around a front of the patient's torso; at least one shoulder strap extending between the back portion and the belt; at least one first strap slide configured to attach the at least one shoulder strap to the back portion; and at least one second strap slide configured to provide length adjustment to the at least one shoulder strap. The at least one first strap slide and the at least one second strap slide each can comprise a coated metal material and are configured to have a low profile, provide high coverage of the at least one should strap and a comfortable feel to feel to the patient, and facilitate physical manipulation and length adjustment of the at least one shoulder strap.

The at least one first strap slide and the at least one second strap slide can comprise a steel material with a nylon coating applied thereto.

The at least one first strap slide and the at least one second strap slide can have a color complementary to a color of a fabric of the support garment.

The at least one first strap slide can comprise straight sides. The at least one first strap slide can have a width of approximately 25 mm-35 mm, more particularly approximately 28 mm-30 mm, more particularly approximately 28.8 mm. The at least one first strap slide can have a height of approximately 10 mm-20 mm, more particularly approximately 13 mm-14 mm, more particularly approximately 13.6 mm. The at least one first strap slide can have a thickness of approximately 1 mm-2 mm, more particularly approximately 1.1 mm-1.7 mm, more particularly approximately 1.4 mm.

The at least one second strap slide can comprise indented sides. The at least one second strap slide can have a width of approximately 25 mm-35 mm, more particularly approximately 28 mm-30 mm, more particularly approximately 28.8 mm. The at least one second strap slide can have a height of approximately 10 mm-20 mm, more particularly approximately 15 mm-17 mm, more particularly approximately 16.1 mm. The at least one second strap slide can have a thickness of approximately 1 mm-2 mm, more particularly approximately 1.0 mm-1.6 mm, more particularly 1.3 mm.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

In an example, a wearable cardiac therapeutic device with an improved mechanism for securing the device on the body of a patient is provided. The device can comprise: a plurality of ECG sensing electrodes configured to sense ECG signals regarding a cardiac function of a patient; a plurality of therapy electrodes to deliver transcutaneous defibrillation shocks or transcutaneous pacing pulses to the patient's heart; and a support garment configured to support and hold the plurality of ECG sensing electrodes and the plurality of therapy electrodes against the patient's body. The support garment can comprise: a back portion; a belt defined by side portions extending from the back portion and around a front of the patient's torso; and a closure mechanism configured to connect the side portions at the front of the patient's torso. The closure mechanism can comprise: a first clasp member disposed on one of the side portions; and a second clasp member disposed on another of the side portions, the second clasp member being identical to the first clasp member. The first and second clasp members are configured to form a mating engagement with each other to secure the side portions. The first and second clasp members are configured to facilitate mutual alignment and securing of the side portions at the front of the patient, provide tactile feedback to a user that the clasp members are matingly engaged, and have an appealing aesthetic appearance.

At least one of the first and second clasp members can be connected to the respective side portion by a belt attachment and adjustable slider.

The device can further comprise a third clasp member disposed on the same side portion as the first clasp member at a different location along a length of the side portion, the third clasp member being identical to the first clasp member and the second clasp member and being configured to form a mating with the second clasp member to secure the side portions.

The first clasp member and the second clasp member can comprise corresponding protrusion and recess features configured to indicate proper alignment of the clasp members to form the mating engagement and to engage each other to secure the clasp members in the mating engagement. The corresponding protrusion and recess features are also configured to snap together to provide the tactile feedback to the user.

The first clasp member and the second clasp member can each comprise at least one smooth-textured protrusion disposed on a rough-textured exterior surface, the smooth-textured protrusions being configured to align with each other to indicate proper alignment of the clasp members to form the mating engagement.

The first clasp member and the second clasp member can each have a color complementary to a color of a fabric of the support garment.

The closure mechanism can have a height of approximately 40 mm-50 mm, more particularly approximately 45 mm-47 mm, more particularly 45.75 mm. The closure mechanism can have a width of approximately 20 mm-35 mm when the first and second clasp members form the mating engagement, more particularly approximately 26 mm-28 mm, more particularly 27.2 mm. The closure mechanism can have a maximum thickness of approximately 3 mm-8 mm, more particularly approximately 5 mm-6 mm, more particularly approximately 5.75 mm.

The device can further comprise a medical device controller in communication with the plurality of ECG sensing electrodes and the plurality of therapy electrodes and configured to detect a patient event based, at least in part, on the ECG signals sensed by the plurality of ECG sensing electrodes.

The medical device controller is further configured to provide a therapy to the patient via the plurality of therapy electrodes in response to a detection of the patient event.

The patient event detected by the medical device controller can comprise one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

The medical device controller is configured to issue an audible alarm to notify the patient that the patient event has been detected.

The medical device controller can comprise one or more input components configured to receive a response input from the patient.

The one or more input components can comprise at least one of: a response button; a touch screen; an audio detection device; a motion sensor; a contact sensor; a pressure sensor; a gesture recognition component; or a patient physiological sensor.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings.

DETAILED DESCRIPTION OF SOME OF THE EMBODIMENTS

Figure 1:
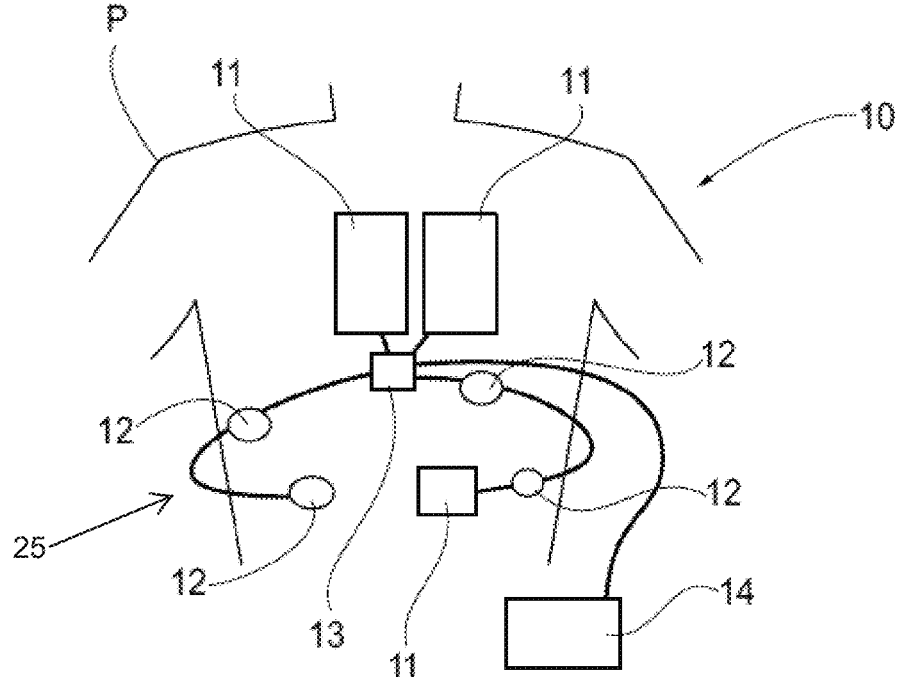
FIG. 1 is a schematic of an exemplary wearable cardiac monitoring and therapeutic medical device that may be used in connection with the present disclosure.

As used herein, the singular forms of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings and described in the following specification are examples. Hence, specific dimensions and other physical characteristics related to the embodiments disclosed herein are not to be considered as limiting.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Also, it should be understood that any numerical range recited herein is intended to include all subranges subsumed therein. For example, a range of "1 to 10" is intended to include any and all subranges between and including the recited minimum value of 1 and the recited maximum value of 10; that is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible.

Figure 19:
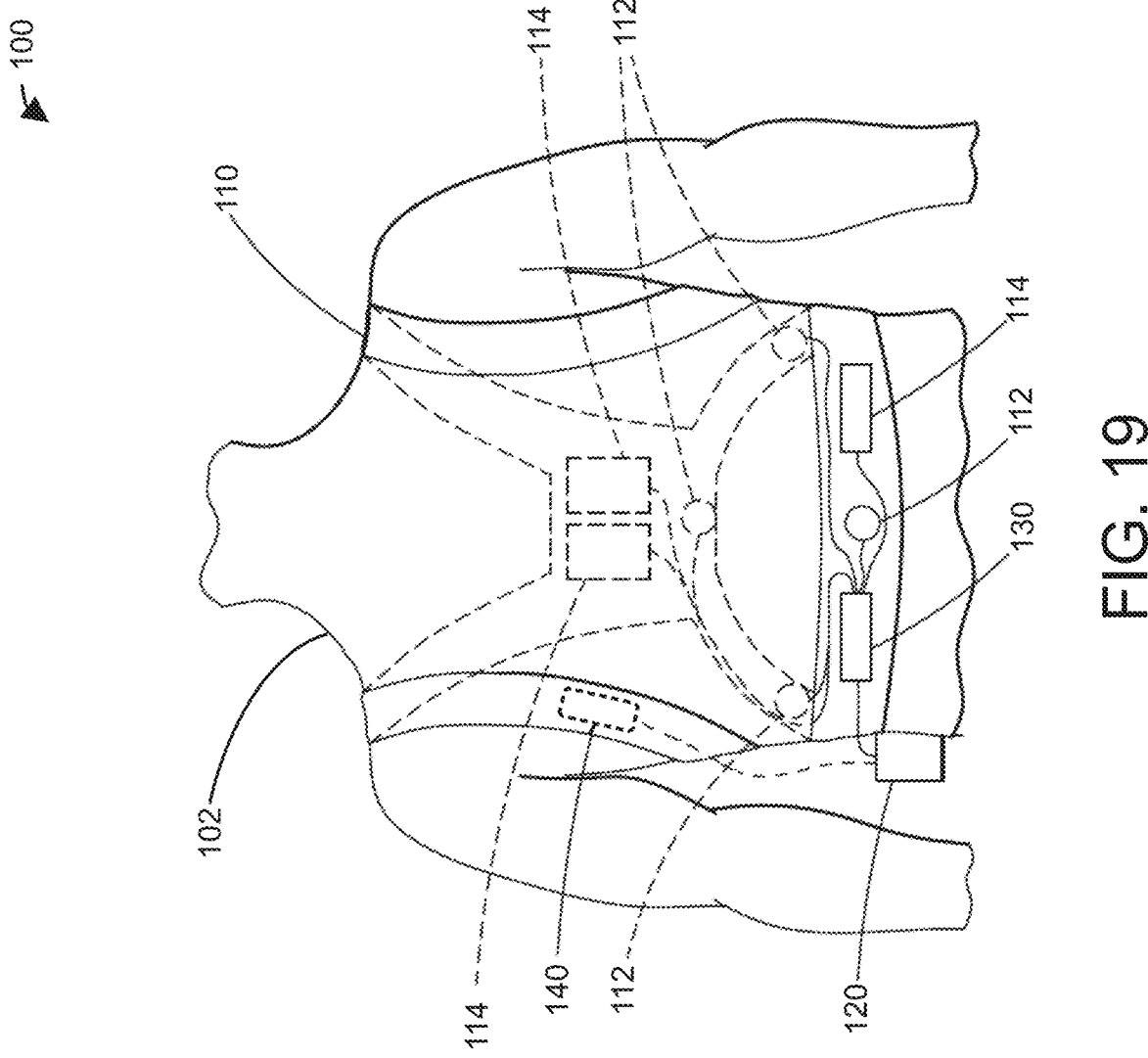
FIG. 19 is a schematic of an exemplary wearable cardiac monitoring and therapeutic medical device that may be used in connection with the present disclosure.

FIG. 1 illustrates an exemplary wearable medical device 10 that is external, ambulatory, and wearable by a patient P and is configured to implement one or more configurations described herein. For example, the wearable medical device 10 can be an external or non-invasive medical device, e.g., the device 10 configured to be located substantially external to the patient P. For example, the wearable medical device 10, shown in FIG. 1 as a wearable defibrillator 10, as described herein can be bodily-attached to the patient such as the LifeVest® wearable cardioverter defibrillator available from ZOLL® Medical Corporation of Pittsburgh, PA and Chelmsford, MA. The wearable defibrillator 10 can be worn or carried by an ambulatory patient P. According to one example of the present disclosure, the wearable defibrillator 10 is used as an ambulatory cardiac monitoring and treatment device within a monitoring and treatment system according to the present disclosure. FIGS. 19-21, discussed in detail below, illustrate in further detail an exemplary wearable medical device 100 that may be used in connection with the present disclosure.

Figure 2:
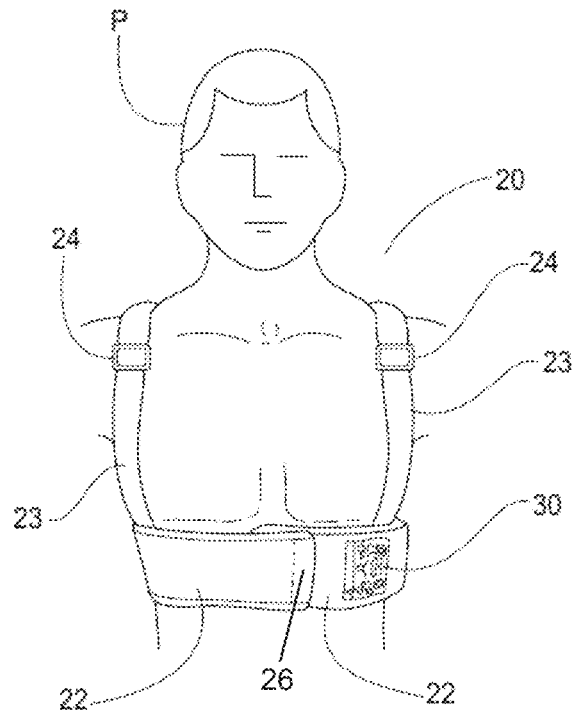
FIG. 2 is a front view of an exemplary support garment for the wearable cardiac monitoring and therapeutic medical device of FIG. 1 as worn on a patient.
Figure 3:
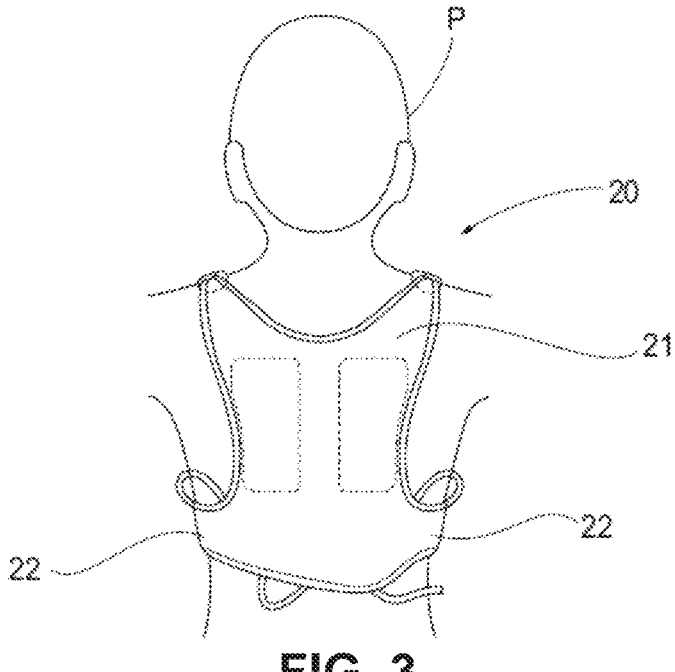
FIG. 3 is a rear view of the support garment of FIG. 2 as worn on a patient.

In accordance with one or more examples, a support garment 20 is provided to keep the electrodes 11 and sensing electrodes 12 in place against the patient's body while remaining comfortable during wear. FIGS. 2 and 3 illustrate such a support garment 20 in accordance with an example of the present disclosure. Such an exemplary support garment is described in U.S. Pat. No. 9,782,578 titled "Patient-worn Energy Delivery Apparatus and Techniques for Sizing Same", the content of which is hereby incorporated by reference.

In order to obtain a reliable ECG signal so that the monitor can function effectively and reliably, the sensing electrodes 12 must be in the proper position and in good contact with the patient's skin. The electrodes 12 need to remain in a substantially fixed position and not move excessively or lift off the skin's surface. If there is excessive movement or lifting, the ECG signal will be adversely affected with noise and can cause problems with the arrhythmia detection and in the ECG analysis and monitoring system. Similarly, in order to effectively deliver the defibrillating energy, the therapy electrodes 11 must be in the proper position and in good contact with the patient's skin. If the therapy electrodes 11 are not firmly positioned against the skin, there can be problems with high impedance, leading to a less effective delivery of energy. If the therapy electrodes 11 are not firmly positioned, there can also be damage to the patient's skin, such as burning, when the shock is delivered.

In accordance with one or more examples, the support garment 20 may provide comfort and functionality under circumstances of human body dynamics, such as bending, twisting, rotation of the upper thorax, semi-reclining, and lying down. These are also positions that a patient may assume if he/she were to become unconscious due to an arrhythmic episode. The design of the garment 20 is generally such that it minimizes bulk, weight, and undesired concentrations of force or pressure while providing the necessary radial forces upon the treatment and sensing electrodes 11, 12 to ensure device functionality. A wearable defibrillator monitor 14 may be disposed in a support holster (not shown) operatively connected to or separate from the support garment 20. The support holster may be incorporated in a band or belt worn about the patient's waist or thigh.

As shown in FIGS. 2 and 3, the support garment 20 may be provided in the form of a vest or harness having a back portion 21 and sides extending around the front of the patient P to form a belt 22. The ends of the belt 22 are connected at the front of the patient P by a closure 26, which may comprise one or more clasps. In some examples, multiple corresponding closures may be provided along the length of the belt 22 to allow for adjustment in the size of the secured belt 22 in order to provide a more customized fit to the patient P. The support garment 20 may further include two straps 23 connecting the back portion 21 to the belt 22 at the front of the patient P. The straps 23 have an adjustable size to provide a more customized fit to the patient P. The straps 23 may be provided with sliders 24 to allow for the size adjustment of the straps 23. The straps 23 may also be selectively attached to the belt 22 at the front of the patient P. The support garment 20 may be comprised of an elastic, low spring rate material that stretches appropriately to keep the electrodes 11, 12 in place against the patient's skin while the patient P moves and is lightweight and breathable. For example, the support garment 20 may have elastic, low spring rate material composition based on a fiber content of about 20% elastic fiber, 32% polyester fiber, and up to 48% or more of nylon or other fiber. Appropriate materials for the support garment 20 are discussed in detail in the above-mentioned U.S. Pat. No. 9,782,578, which is incorporated by reference herein.

In accordance with one or more examples, the support garment 20 may be formed from an elastic, low spring rate material and constructed using tolerances that are considerably closer than those customarily used in garments. The materials for construction are chosen for functionality, comfort, and biocompatibility. The materials may be configured to wick perspiration from the skin. The support garment 20 may be formed from one or more blends of nylon, polyester, and spandex fabric material. Different portions or components of the support garment 20 may be formed from different material blends depending on the desired flexibility and stretchability of the support garment 20 and/or its specific portions or components. For instance, the belt 22 of the support garment 20 may be formed to be more stretchable than the back portion 21. According to one example, the support garment 20 is formed from a blend of nylon and spandex materials, such as a blend of 77% nylon and 23% spandex. According to another example, the support garment 20 is formed from a blend of nylon, polyester, and spandex materials, such as 40% nylon, 32% polyester, and 14% spandex. According to another example, the support garment 20 is formed from a blend of polyester and spandex materials, such as 86% polyester and 14% spandex or 80% polyester and 20% spandex. For example, the nylon and spandex material is configured to be aesthetically appealing, and comfortable, e.g., when in contact with the patient's skin. Stitching within the support garment 20 may be made with industrial stitching thread. According to one example, the stitching within the support garment 20 is formed from a cotton-wrapped polyester core thread.

FIGS. 4A-18 illustrate an exemplary support garment 50 according to the present disclosure. The support garment 50 incorporates additional improvements for enhancing the patient's experience in wearing the support garment for an extended period of time. The support garment examples provided herein can promote one or more of the following: comfort, aesthetic appearance, and ease of use or application for older patients, or patients with physical infirmities and/or who are physically challenged, including patients with rheumatic conditions, patients with arthritis, and/or patients with autoimmune or inflammatory diseases that affect joints, tendons, ligaments, bones, and muscles of the arm and hand. Patients afflicted with such conditions can properly and/or correctly don the garments described herein. Features of the support garments may also help minimize the time needed by patients to assemble, don or remove the support garment. Further, patients benefit from such features, which can facilitate longer wear times, better patient compliance, and/or improve the reliability of the detected physiological signals and treatment of the patient. These features promote ease of use, comfort and/or an aesthetic appearance for such patient populations, and comprise or consist of one or more, or all of: circular hook and loop fasteners, finger loops, flat lock stitching, plastic snaps configured within a predetermined force range, a gray color and/or appearance, antimicrobial treatment, nylon and/or spandex edge binding, garment straps with double plush material, nylon coated steel tri-glides, and/or a butterfly clasp fastener, or any combination thereof.

In some examples the support garment 50 can comprise circular hook and loop fasteners, and optionally one or more of the following features: finger loops, flat lock stitching, plastic snaps configured within a predetermined force range, a gray color and/or appearance, antimicrobial treatment, nylon and/or spandex edge binding, garment straps with double plush material, nylon coated steel tri-glides, and/or a butterfly clasp fastener. In other examples, the support garment 50 can comprise finger loops, and optionally one or more of the following features: circular hook and loop fasteners, flat lock stitching, plastic snaps configured within a predetermined force range, a gray color and/or appearance, antimicrobial treatment, nylon and/or spandex edge binding, garment straps with double plush material, nylon coated steel tri-glides, and/or a butterfly clasp fastener. In other examples, the support garment 50 can comprise flat lock stitching, and optionally one or more of the following features: circular hook and loop fasteners, finger loops, plastic snaps configured within a predetermined force range, a gray color and/or appearance, antimicrobial treatment, nylon and/or spandex edge binding, garment straps with double plush material, nylon coated steel tri-glides, and/or a butterfly clasp fastener. In other examples, the support garment 50 can comprise plastic snaps configured within a predetermined force range, and optionally one or more of the following features: circular hook and loop fasteners, finger loops, flat lock stitching, a gray color and/or appearance, antimicrobial treatment, nylon and/or spandex edge binding, garment straps with double plush material, nylon coated steel tri-glides, and/or a butterfly clasp fastener. In other examples, the support garment 50 can comprise a gray color and/or appearance, and optionally one or more of the following features: circular hook and loop fasteners, finger loops, flat lock stitching, plastic snaps configured within a predetermined force range, antimicrobial treatment, nylon and/or spandex edge binding, garment straps with double plush material, nylon coated steel tri-glides, and/or a butterfly clasp fastener. In other examples, the support garment 50 can comprise antimicrobial treatment, and optionally one or more of the following features: circular hook and loop fasteners, finger loops, flat lock stitching, plastic snaps configured within a predetermined force range, a gray color and/or appearance, nylon and/or spandex edge binding, garment straps with double plush material, nylon coated steel tri-glides, and/or a butterfly clasp fastener. In other examples, the support garment 50 can comprise nylon and/or spandex edge binding, and optionally one or more of the following features: circular hook and loop fasteners, finger loops, flat lock stitching, plastic snaps configured within a predetermined force range, a gray color and/or appearance, antimicrobial treatment, garment straps with double plush material, nylon coated steel tri-glides, and/or a butterfly clasp fastener. In other examples, the support garment 50 can comprise nylon and/or spandex edge binding, and optionally one or more of the following features: circular hook and loop fasteners, finger loops, flat lock stitching, plastic snaps configured within a predetermined force range, a gray color and/or appearance, antimicrobial treatment, garment straps with double plush material, nylon coated steel tri-glides, and/or a butterfly clasp fastener. In other examples, the support garment 50 can comprise garment straps with double plush material, and optionally one or more of the following features: circular hook and loop fasteners, finger loops, flat lock stitching, plastic snaps configured within a predetermined force range, a gray color and/or appearance, antimicrobial treatment, nylon and/or spandex edge binding, garment straps with double plush material, nylon coated steel tri-glides, and/or a butterfly clasp fastener. In other examples, the support garment 50 can comprise nylon coated steel tri-glides, and optionally one or more of the following features: circular hook and loop fasteners, finger loops, flat lock stitching, plastic snaps configured within a predetermined force range, a gray color and/or appearance, antimicrobial treatment, nylon and/or spandex edge binding, garment straps with double plush material, and/or a butterfly clasp fastener. In other examples, the support garment 50 can comprise a butterfly clasp fastener, and optionally one or more of the following features: circular hook and loop fasteners, finger loops, flat lock stitching, plastic snaps configured within a predetermined force range, a gray color and/or appearance, antimicrobial treatment, nylon and/or spandex edge binding, garment straps with double plush material, and/or nylon coated steel tri-glides. In other examples the support garment 50 can comprise or consist of all of the following: circular hook and loop fasteners, finger loops, flat lock stitching, plastic snaps configured within a predetermined force range, a gray color and/or appearance, antimicrobial treatment, nylon and/or spandex edge binding, garment straps with double plush material, nylon coated steel tri-glides, and a butterfly clasp fastener.

In some examples, selected combinations of one or more, or all, of the following features (1) circular hook and loop fasteners, (2) finger loops, (3) flat lock stitching, (4) plastic snaps configured within a predetermined force range, (5) a gray color and/or appearance, (6) antimicrobial treatment, (7) nylon and/or spandex edge binding, (8) garment straps with double plush material, (9) nylon coated steel tri-glides, and/or a (10) butterfly clasp fastener can be used in a support garment 50. For example, features (1) and (2), or features (1)-(3), or features (1)-(4), or features (1)-(7), or features (2) and (3), or features (7)-(10), or features (1) and (10), or all of features (1)-(10), or any combination of one or more of features (1)-(10), can be included in a support garment 50, as desired.

In some examples, a garment for a wearable therapeutic device in accordance with this disclosure can comprise or consist of one or more of, or all of, the following features:

circular hook-and-loop fastener patches configured to facilitate alignment and assembly of the respective ECG sensing electrodes on the support garment and provide for fastening and support for the respective ECG sensing electrodes on the support garment independent of the rotational orientation of the respective ECG sensing electrodes; and/or a plurality of handling tab members, at least one handling tab member being fastened to each of the plurality of support pockets, the handling tab members being configured to facilitate opening and closing of the plurality of support pockets for assembly of the plurality of therapy electrodes therein, wherein each of the handling tab members comprises a fabric tape formed in a loop extending from an outer surface of a respective one of the plurality of support pockets to an inner surface of the respective support pocket, and wherein each of the handling tab members has a length and width configured to facilitate physical manipulation of the handling tab member by grasping the handling tab member and/or inserting a finger into the loop; and/or a back portion; and a belt defined by side portions extending from the back portion and around a front of the patient's torso, wherein the back portion and the side portions defining the belt are secured by a seam formed by aesthetic flatlock stitching; and/or a plurality of plastic snaps for fastening the plurality of support members on the support garment to secure the distribution box and the plurality of therapy electrodes on the support garment, at least one plastic snap being provided to fasten each of the plurality of support members, wherein each of the plurality of plastic snaps is configured to facilitate physical manipulation and fastening or unfastening of a respective support member and provide tactile feedback when the plastic snaps are secured; and/or the support garment comprising a gray color fabric material; and/or the support garment comprising a fabric having an antimicrobial treatment applied thereto, wherein the antimicrobial treatment is configured to limit or prevent odor and bacterial growth on the support garment; and/or the support garment comprising an aesthetic edge binding surrounding at least a portion of a periphery of the support garment, the aesthetic edge binding comprising nylon and spandex materials; and/or a back portion; a belt defined by side portions extending from the back portion and around a front of the patient's torso; and at least one shoulder strap extending between the back portion and the belt, the at least one shoulder strap comprising a double plush elastic material; and/or a back portion; a belt defined by side portions extending from the back portion and around a front of the patient's torso; at least one shoulder strap extending between the back portion and the belt; at least one first strap slide configured to attach the at least one shoulder strap to the back portion; and at least one second strap slide configured to provide length adjustment to the at least one shoulder strap, wherein the at least one first strap slide and the at least one second strap slide each comprise a coated metal material and are configured to have a low profile, provide high coverage of the at least one should strap and a comfortable feel to feel to the patient, and facilitate physical manipulation and length adjustment of the at least one shoulder strap; and/or a back portion; a belt defined by side portions extending from the back portion and around a front of the patient's torso; and a closure mechanism configured to connect the side portions at the front of the patient's torso, the closure mechanism comprising: a first clasp member disposed on one of the side portions; and a second clasp member disposed on another of the side portions the second clasp member being identical to the first clasp member, wherein the first and second clasp members are configured to form a mating engagement with each other to secure the side portions, and wherein the first and second clasp members are configured to facilitate mutual alignment and securing of the side portions at the front of the patient, provide tactile feedback to a user that the clasp members are matingly engaged, and have an appealing aesthetic appearance.

For example, the garments described herein generally follow design principles as noted below (e.g., similar to those prescribed in the Arthritis Foundation Guidelines).

Removing, donning, and assembling the garment and associated components do not require fine motor control or simultaneous actions, Replacing electrodes and other components is possible for patients with limited reach and strength, The garment and/or components include surface and/or textural aspects that makes the garment and/or components easy to grip and control.

The garment and/or components include features designed to minimize simultaneous actions such as depressing and pulling, and/or The garment and/or components include features to provide positive feedback (for example, "snap", "click", among others).

These features can encourage patients to wear the support garment and associated medical device for longer and/or continuous periods of time with minimal interruptions in the periods of wear. For example, by minimizing interruptions in periods of wear and/or promoting longer wear durations, patients and caregivers can be assured that the device is providing desirable information as well as protection from adverse cardiac events such as ventricular tachycardia and/or ventricular fibrillation, among others. Moreover, when the patient's wear time and/or compliance is improved, the device can collect information on arrhythmias that are not immediately life-threatening, but may be useful to monitor for the patient's cardiac health. Such arrhythmic conditions can include onset and/or offset of bradycardia, tachycardia, atrial fibrillation, pauses, ectopic beats bigeminy, trigeminy events among others. For instance, episodes of bradycardia, tachycardia, or atrial fibrillation can last several minutes and/or hours. The support garments herein provide features that encourage patients to keep the device on for longer and/or uninterrupted periods of time, thereby increasing the quality of data collected about such arrhythmias. Additionally, features as described herein, including, circular hook and loop fasteners, finger loops, flat lock stitching, plastic snaps configured within a predetermined force range, a gray color and/or appearance, antimicrobial treatment, nylon and/or spandex edge binding, garment straps with double plush material, nylon coated steel tri-glides, and/or a butterfly clasp fastener promotes better patient compliance resulting in lower false positives and noise in the physiological signals collected from ECG electrodes and other sensors disposed within the support garment. For example, when patients wear the device for longer and/or uninterrupted periods of time, the device tracks cardiac events and distinguishes such events from noise over time.

The improvements incorporated in the support garment 50 may provide comfort and wearability to the patient by utilizing softer materials for at least some of the components of the support garment and by utilizing materials and construction features that are less likely to dig into and/or rub on the patient's skin in a painful or irritating manner. The improvements incorporated in the support garment 50 may provide a more attractive aesthetic appearance by incorporating coloring and other visual features that give the support garment 50 the appearance of sportswear, activewear, or fitted athletic clothing. The improvements incorporated in the support garment 50 may provide improved overall cleanliness and maintain a cleaner appearance over time by incorporating coloring that can be maintained over extensive use and wash cycles and limit the appearance of stains or dinginess that can be acquired over extensive use of a garment, as well as by incorporating anti-microbial features. The improvements incorporated in the support garment 50 may further ease and facilitate including, adding, assembling, and/or fastening the components of the wearable medical device 14, 100 on the support garment 50 by providing more reliable/durable fastening mechanisms that can be more easily aligned and manipulated. The improvements incorporated in the support garment 50 may also further ease and facilitate fastening of the support garment 50 on the patient's body by providing closure mechanisms and tightening mechanisms that can be more easily fastened and/or manipulated.

In accordance with one or more examples, the support garment 50 is provided to keep the electrodes 11, 12 of an electrode assembly 25 associated with a wearable cardiac therapeutic device in place against the patient's body while remaining comfortable to wear. In particular, the electrode assembly 25 may include a plurality of ECG sensing electrodes 12 configured to sense ECG signals regarding a cardiac function of the patient and a plurality of therapy electrodes 11 configured to deliver transcutaneous defibrillation shocks or transcutaneous pacing pulses to the patient's heart. Examples of the wearable cardiac therapeutic devices in which the support garment 50 may be utilized include the wearable medical device 14 described above with reference to FIG. 1 and the wearable medical device 100 described in detail below with reference to FIGS. 19-21. It is to be appreciated that the support garment 50 described herein may be utilized in connection with a wearable medical device of any suitable type or configuration.

Figure 4A:
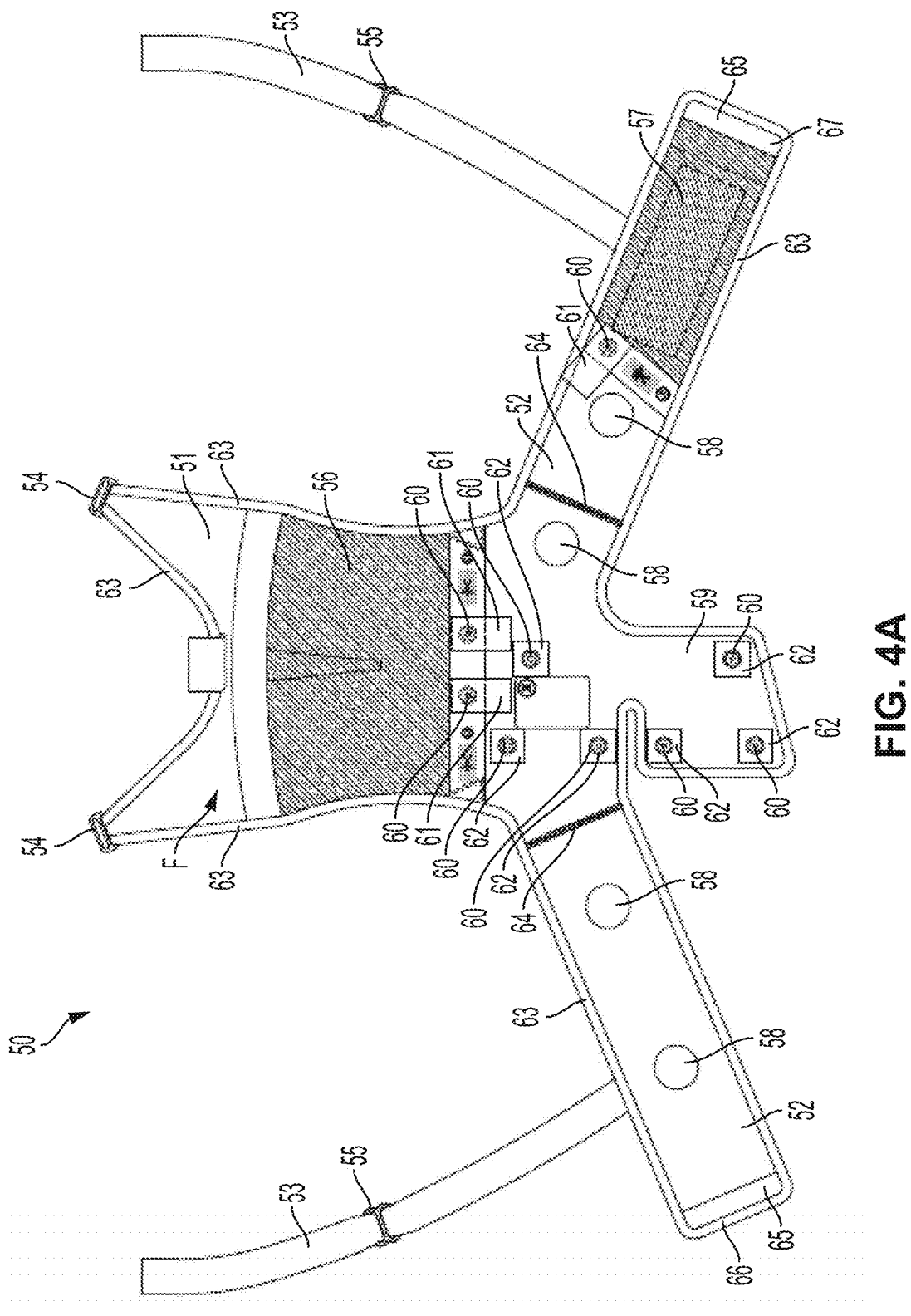
FIGS. 4A and 4B are a front view of an exemplary support garment and electrode assembly for the wearable monitoring and therapeutic medical device that may be used in connection with the present disclosure.
Figure 4B:
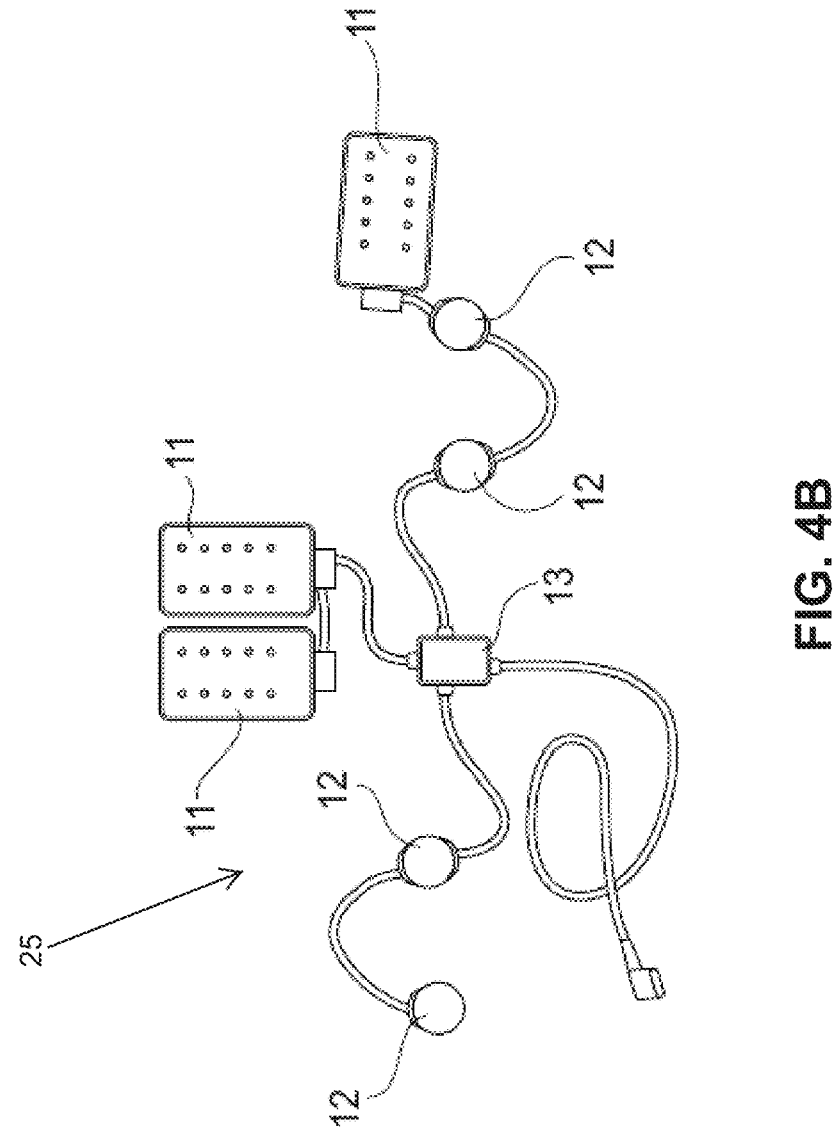

As shown in FIGS. 4A and 4B, the support garment 50 may be provided in the form of a vest or harness having a back portion 51 and sides extending around the front of the patient to form a belt 52. The ends 66, 67 of the belt 52 are connected at the front of the patient by a closure mechanism 65. The support garment 50 may further include two straps 53 connecting the back portion 51 to the belt 52 at the front of the patient. The straps 53 have an adjustable size to provide a more customized fit to the patient. The straps 53 may also be selectively attached to the belt 22 at the front of the patient. The support garment 50 may be comprised of an elastic, low spring rate fabric material F that stretches appropriately to keep the electrodes 11, 12 in place against the patient's skin and is lightweight and breathable. The component materials of the fabric material F may be chosen for functionality, comfort, and biocompatibility. The component materials may be configured to wick perspiration from the skin. For example, the fabric material F may comprise a tricot fabric, the tricot fabric comprising nylon and spandex materials. The tricot fabric may comprise approximately 65%-90% nylon material, more particularly 70%-85% nylon material, more particularly 77% nylon material. It is to be appreciated that the fabric material F chosen for the support garment 50 may be comprised of any suitable materials or combinations of materials.

The support garment 50 may be configured for one-sided assembly of the electrode assembly 25 onto the support garment 50 such that the support garment 50 does not need to be flipped or turned over in order to properly position the therapy electrodes 11 and the sensing electrodes 12 on the support garment 50. The inside surface of the back portion 51 of the support garment 50 includes pocket(s) 56 for receiving one or two therapy electrodes 11 to hold the electrode(s) 11 in position against the patient's back. The pocket 56 is made from a non-elastic, conductive mesh fabric designed to isolate the metallic therapy electrode(s) 11 from the skin of the patient while allowing a conductive gel that may be automatically extruded from the electrode(s) 11 to easily pass through. The forces applied to the electrode(s) 11 by the fabric, in addition to the use of the conductive gel, may help ensure that proper contact and electrical conductivity with the patient's body are maintained, even during body motions. The fabric material of the pocket(s) 56 also maintains electrical contact between the electrode(s) 11 through the mesh material before the conductive gel is dispensed, which allows for monitoring of the therapy electrode(s) 11 to ensure that the electrode(s) 11 are positioned against the skin such that a warning may be provided by the wearable defibrillator 14 if the therapy electrode(s) 11 is not properly positioned. Another pocket 57 made from the same non-elastic, conductive mesh fabric is included on an inside surface of the belt 52 for receiving a therapy electrode 11 and holding the electrode 11 in position against the patient's left side. According to one example, the pockets 56, 57 are formed from an electrically conductive knit material. The material of the pockets 56, 57 may have a metal coating, such as a silver coating, applied thereto to provide electrical conductivity. The pockets 56, 57 may be closed by snaps 60.

The back portion 51 and the belt 52 of the support garment 50 may further comprise attachment points 58 for supporting the sensing electrodes 12 in positions against the patient's skin in spaced locations around the circumference of the patient's chest. The attachment points 58 may include hook-and-loop fasteners for attaching electrodes 12 having a corresponding fastener disposed thereon to the inside surface of the belt 52. The attachment points 58 may be color coded to provide guidance for appropriately connecting the sensing electrodes 12 to the support garment 50. The support garment 50 may further be provided with a flap 59 extending from the back portion 51. The flap 59 and the back portion 51 include snaps 60 for connecting the flap 59 to the inside surface of the back portion 51 in order to define a pouch or pocket for holding a distribution box 13 of the electrode assembly 25. The outer surface of the belt 52 may incorporate a schematic 30 (shown in FIG. 2) imprinted on the fabric for assisting the patient or medical professional in assembling the electrode assembly 25 onto the support garment 50.

Further discussion of the additional improvements incorporated into the support garment 50 for enhancing the patient's experience in wearing the support garment 50 for an extended period of time according to one or more examples of the present disclosure is provided below with reference to FIGS. 4A-18.

Figure 5:
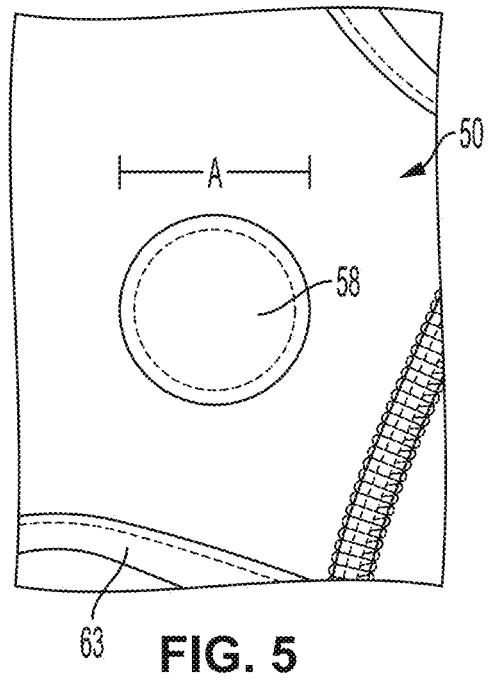
FIG. 5 is an enlarged view of a fastener for an ECG sending electrode on the support garment of FIGS. 4A and 4B that may be used in connection with the present disclosure.

With reference to FIGS. 4A, 4B, and 5, according to an example of the present disclosure, the support garment 50 may be incorporated into a wearable cardiac therapeutic device with improved fasteners for fastening and supporting electrodes on the support garment 50.

The device includes a plurality of ECG sensing electrodes 12 configured to sense ECG signals regarding a cardiac function of the patient and the support garment 50 configured to support and hold the plurality of ECG sensing electrodes 12 against the patient's body. The device may further include a plurality of therapy electrodes 11 configured to deliver transcutaneous defibrillation shocks or transcutaneous pacing pulses to the patient's heart. The support garment 50 may be configured to support and hold the plurality of therapy electrodes 11 against the patient's body. The support garment 50 includes a plurality of fasteners/attachment points 58 on an inside surface thereof for fastening and supporting the plurality of ECG sensing electrodes 12 on the support garment 50.

Each of the plurality of fasteners/attachment points 58 includes a circular hook-and-loop fastener patch permanently affixed to a predetermined location on the inside surface of the support garment 50. Each of the plurality of ECG sensing electrodes 12 includes a corresponding hook-and-loop fastener configured to connect to a respective circular hook-and-loop fastener patch on the support garment 50.

The circular hook-and-loop fastener patches are configured to facilitate alignment and assembly of the respective ECG sensing electrodes 12 on the support garment 50 and to provide for fastening and support for the respective ECG sensing electrodes 12 on the support garment independent of the rotational orientation of the respective ECG sensing electrodes 12. This provides for easier assembly of the ECG sensing electrodes 12 on the support garment 50 and less error with respect to the assembly of the ECG sensing electrodes 12 on the support garment 50 resulting from misalignment of the hook-and-loop fasteners on the ECG sensing electrodes 12 with the hook-and-loop fastener patches of the fasteners/attachment points 58 on the support garment 50.

According to an example, each of the circular hook-and-loop fastener patches has a diameter A of approximately 0.5"-3.0". According to another example, each of the circular hook-and-loop fastener patches has a diameter of approximately 1.25". It is to be appreciated that the circular hook-and-loop fastener patches may be of any suitable size.

According to an example, the circular hook-and-loop fastener patches comprise a nylon, polyester, or polypropylene material. It is to be appreciated that the circular hook-and-loop fastener patches may comprise any suitable materials.

According to an example, the circular hook-and-loop fastener patches are permanently affixed to the interior surface of the support garment 50 by sewing. It is to be appreciated that the circular hook-and-loop fastener patches may be affixed to the support garment 50 by any suitable technique.

The circular hook-and-loop fastener patches of the fasteners/attachment points 58 and the corresponding hook-and-loop fasteners on the respective ECG sensing electrodes 12 may be color coded to facilitate assembly of each of the plurality of ECG sensing electrodes 12 to a corresponding predetermined location/attachment point 58 on the inside surface of the support garment 50. For instance, the circular hook-and-loop fastener patches of the fasteners/attachment points 58 may be individually colored yellow, blue, red, and brown. Each of the ECG sensing electrodes 12 may include a hook-and-loop fastener having a corresponding yellow, blue, red, and brown color so that the patient may assemble the plurality of ECG sensing electrodes 12 to the correct location/attachment point 58 on the support garment 50 by matching the colors of the hook-and-loop fasteners on the ECG sensing electrodes 12 with the colors of the hook-and-loop fastener patches on the support garment 50. The yellow, blue, red, and brown colors discussed above are exemplary. The circular hook-and-loop fastener patches on the support garment 50 and corresponding hook-and-loop fasteners on the ECG sensing electrodes 12 may be of any color suitable for the above-discussed color coding.

Figure 6:
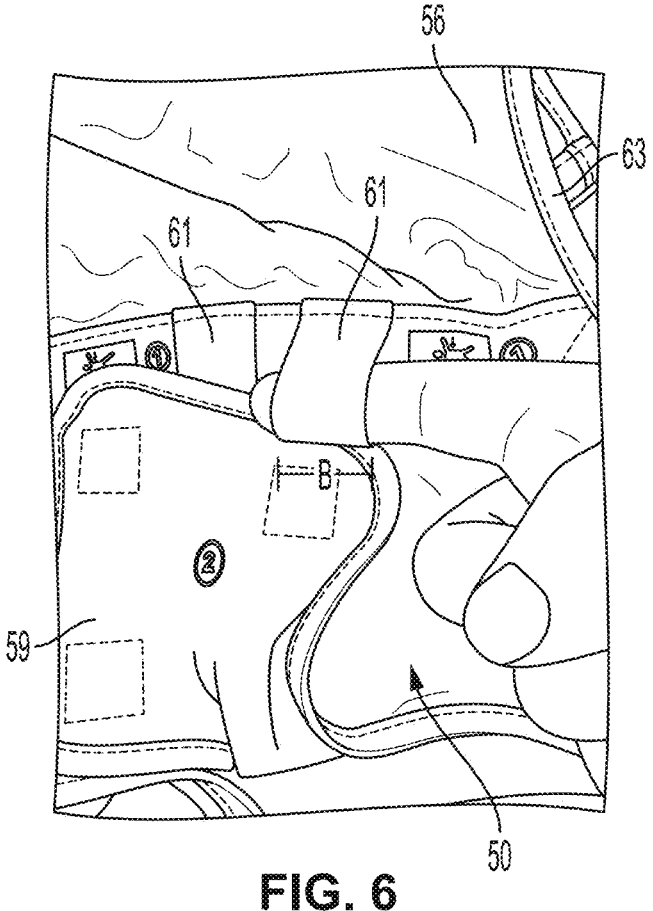
FIG. 6 is an enlarged view of a handling tab member for a support pocket on the support garment of FIGS. 4A and 4B that may be used in connection with the present disclosure.

With reference to FIGS. 4A, 4B, and 6, according to an example of the present disclosure, the support garment 50 may be incorporated into a wearable cardiac therapeutic device with improved features for assembly of therapy electrodes 11 on the support garment 50.

The device includes a plurality of therapy electrodes 11 configured to deliver transcutaneous defibrillation shocks or transcutaneous pacing pulses to a patient's heart and the support garment 50 configured to support and hold the plurality of therapy electrodes 11 against the patient's body. The device may further include a plurality of ECG sensing electrodes 12 configured to sense ECG signals regarding a cardiac function of the patient. The support garment 50 may be configured to support and hold the plurality of ECG sensing electrodes 12 against the patient's body.

The support garment 50 includes a plurality of support pockets 56, 57 disposed on an inside surface of the support garment 50 for supporting the plurality of therapy electrodes 11 on the support garment 50 and a plurality of handling tab members 61. At least one handling tab member 61 is fastened to each of the plurality of support pockets 56, 57. The handling tab members 61 are configured to facilitate opening and closing of the plurality of support pockets 56, 57 for assembly of the plurality of therapy electrodes 11 therein.

Each of the handling tab members 61 includes a fabric tape formed in a loop extending from an outer surface of a respective one of the plurality of support pockets 56, 57 to an inner surface of the respective support pocket 56, 57. Each of the handling tab members 61 has a length and width configured to facilitate physical manipulation of the handling tab member by grasping the handling tab member and/or inserting a finger into the loop. Accordingly, the handling tab members 61 may be more easily grasped by hand or have a finger inserted therein to manipulate an end of the respective support pocket 56, 57 so that the support pocket 56, 57 may be more easily opened to allow insertion and/or removal of a respective therapy electrode 11 therein. The handling tab members 61 provide for multiple uses during assembly and disassembly of the therapy electrodes 11 from the support pockets 56, 57 and accommodate a greater range of finger sizes within the loop.

According to an example, the fabric tape of each of the handling tab members 61 has a width B of approximately 0.5"-1.5", more particularly approximately 1.0", and a length of approximately 5"-10", more particularly approximately 6"-8", more particularly approximately 6.5". It is to be appreciated that the fabric tape of each of the handling tab members 61 may be of any suitable length and width.

According to an example, the fabric tape of each of the handling tab members 61 includes a cotton twill material. It is to be appreciated that the fabric tape may include any suitable material or combination of materials.

According to another example, each of the handling tab members 61 is color coded to correspond to a colored indicator provided on a respective therapy electrode 11. Accordingly, the handling tab members 61 are color coordinated with the indicator provided on the respective therapy electrodes 11 to facilitate appropriate assembly of the therapy electrodes 11 in the support pockets 56, 57. The support pockets 56, 57 may also include matching colored indicators corresponding to the colored indicators on the therapy electrodes 11 and the color of the handling tab members 61. According to an example, the handling tab members 61 have a green color and the therapy electrodes 11 and support pockets 56, 57 include colored indicators of a matching green color.

According to an example, each of the handling tab members 61 is fastened to an open end of the respective support pocket 56, 57 and/or to an at least partially open side of the respective support pocket 56, 57 so that the handling tab members 61 may be manipulated to open the respective support pockets 56, 57 to allow for assembly/disassembly of the therapy electrodes 11 therein. According to an example, each of the handling tab members 61 is fastened to the respective support pocket 56, 57 by stitching one end of the handling tab member 61 to an outside surface of the respective support pocket 56, 57 at an open end or at an at least partially open side and by stitching the opposite end of the handling tab member 61 to an inside surface of the respective support pocket 56, 57. It is to be appreciated that the handling tab members 61 may be fastened to the support pockets 56, 57 in any suitable manner.

According to an example, each of the handling tab members 61 includes an associated snap 60 for releasably securing the respective support pocket 56, 57 in a closed condition. The handling tab member 61 may have a female plastic snap member 601 or a male plastic snap member 604 disposed thereon configured to form a mating engagement with a counterpart male plastic snap member 604 or female plastic snap member 601 disposed on an inside surface of the support garment 50 to releasably secure the respective support pocket 56, 57 in the closed condition. The mating engagement between the plastic snap members 601, 604 may be disengaged to open the respective support pocket 56, 57. The counterpart plastic snap members 601, 604 may be disposed on a piece fabric tape (not shown) affixed, such as by sewing, to the interior surface of the support garment 50. The piece of fabric tape may be of the same material and color as the fabric tape of the corresponding handling tab member to match the appearance and color coding discussed above.

Figure 7:
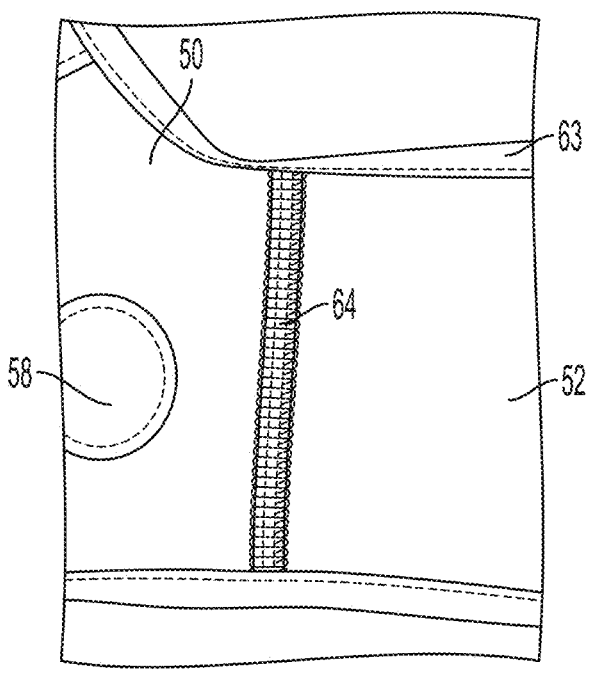
FIG. 7 is an enlarged view of a stitching pattern for fastening components of the support garment of FIGS. 4A and 4B that may be used in connection with the present disclosure.
Figure 8:
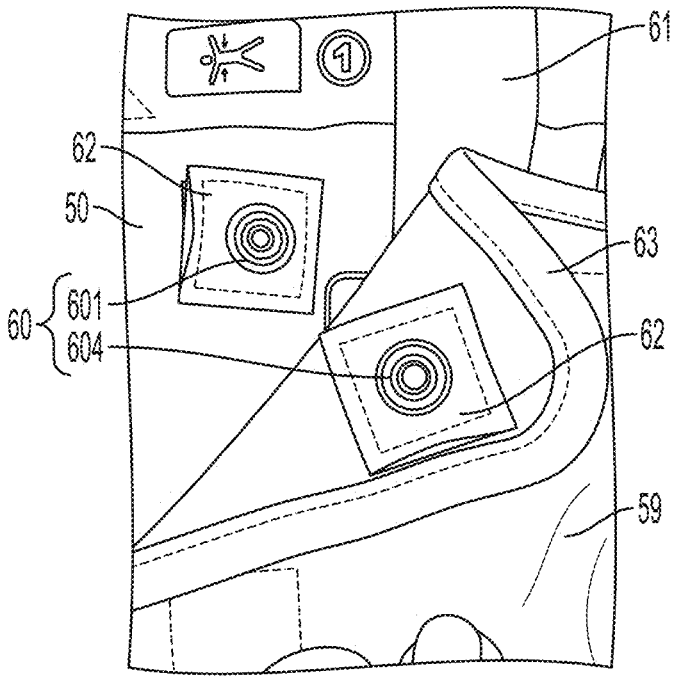
FIG. 8 is an enlarged view of a plastic snap for fastening a support member of the support garment of FIGS. 4A and 4B that may be used in connection with the present disclosure.
Figure 9:
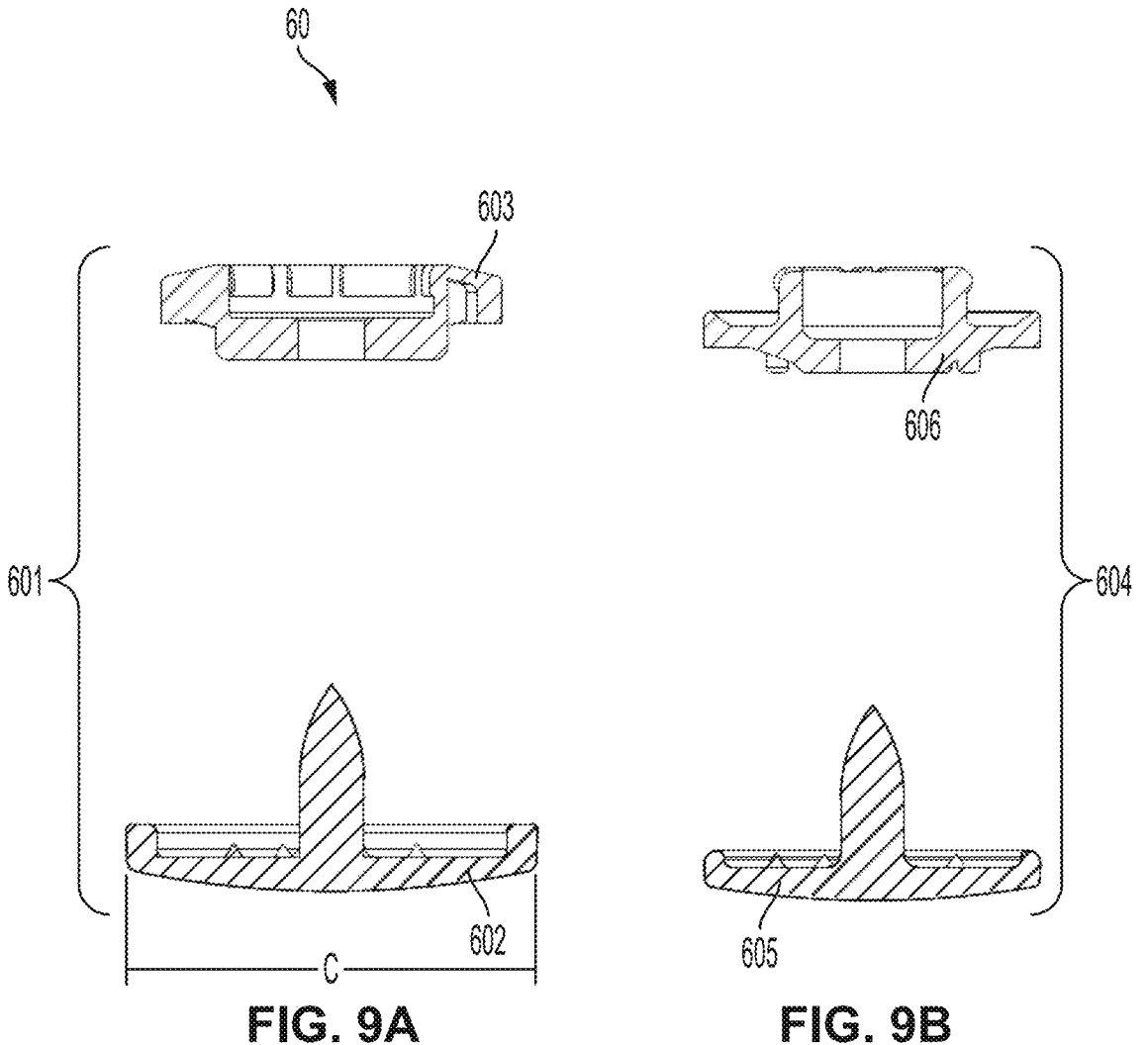
FIGS. 9A and 9B are exploded side views of male and female plastic snap members of the plastic snap of FIG. 8.

With reference to FIGS. 4A, 4B, and 7, according to an example of the present disclosure, the support garment 50 may be incorporated into a wearable cardiac therapeutic device with improved aesthetic features.

The device includes a plurality of ECG sensing electrodes 12 configured to sense ECG signals regarding a cardiac function of a patient, a plurality of therapy electrodes 11 configured to deliver transcutaneous defibrillation shocks or transcutaneous pacing pulses to the patient's heart, and a support garment configured to support and hold the plurality of ECG sensing electrodes 12 and the plurality of therapy electrodes 11 against the patient's body.

The support garment 50 includes a back portion 51 and a belt 52 defined by side portions extending from the back portion 51 and around a front of the patient's torso.

The back portion 51 and the side portions defining the belt 52 are secured by a seam formed by aesthetic flatlock stitching 64. For example, the aesthetic flatlock sticking 64 is configured to have an appealing aesthetic appearance. In one example, the aesthetic flatlock stitching 64 may be incorporated into the support garment 50 to provide the support garment 50 with a more modern and stylized appearance typically associated with sportswear, activewear, and fitted athletic clothing.

According to an example, the aesthetic flatlock stitching 64 conforms to ISO 607.

According to an example, the aesthetic flatlock stitching 64 includes approximately 10-20 stitches per inch, more particularly approximately 12-16 stitches per inch, more particularly approximately 14 stitches per inch. It is to be appreciated that the aesthetic flatlock stitching 64 may include any suitable amount of stitches.

According to an example, the aesthetic flatlock stitching 64 includes two threads sewn together via machine sewing. A first thread may be a textured polyester thread having a size of approximately 18-30 tex, more particularly approximately 22-28 tex, more particularly approximately 24 tex, and a strength of approximately 1 lb.-3 lbs., more particularly approximately 1.5 lbs.-2.5 lbs., more particularly 2.02 lbs. A second thread may be a polyester-wrapped, polyester core thread having a size of approximately 18-30 tex, more particularly 22-28 tex, and more particularly 24 tex, and a strength of approximately 1.5 lbs.-3.5 lbs., more particularly approximately 2.0 lbs.-3.0 lbs., a more particularly 2.77 lbs. The formation of the flatlock stitching 64 and the threading may be configured to provide desirable seam integrity and durability, seam strength, and abrasion resistance, to facilitate machine sewing, to have durable color and chemical resistance, and also to have high elasticity, softness, and a comfortable feel. It is to be appreciated that the aesthetic flatlock stitching 64 may be formed from any suitable threading or combination of threading and may be applied to the support garment via any suitable stitching technique.

According to another example, an aesthetic straight lockstitch may be used to secure the side portions defining the belt 52 to the back portion 51. For example, the aesthetic lockstitch is configured to have an appealing aesthetic appearance. It is to be appreciated that the seam may be of any suitable type and formed according to any suitable stitching technique.

With reference to FIGS. 4A, 4B, and 8-9B, according to an example of the present disclosure, the support garment 50 may be incorporated into a wearable cardiac therapeutic device with improved features of device components on the support garment 50.

The device includes a plurality of therapy electrodes 11 configured to deliver transcutaneous defibrillation shocks or transcutaneous pacing pulses to a patient's heart, a distribution box 13, and a support garment 50 configured to support plurality of therapy electrodes 11 and the distribution box 13 and to hold the plurality of therapy electrodes 11 against the patient's body. The device may further include a plurality of ECG sensing electrodes 12 configured to sense ECG signals regarding a cardiac function of a patient. The support garment may be configured to support and hold the plurality of ECG sensing electrodes 12 against the patient's body.

The support garment 50 includes a plurality of support members disposed on an inside surface of the support garment 50 for supporting the plurality of therapy electrodes 11 and the distribution box 13 on the support garment 50 and a plurality of plastic snaps 60 for fastening the plurality of support members on the support garment 50 to secure the distribution box 13 and the plurality of therapy electrodes 11 on the support garment 50, at least one plastic snap 60 being provided to fasten each of the plurality of support members.

Each of the plurality of plastic snaps 60 is configured to facilitate physical manipulation and fastening or unfastening of a respective support member and to provide tactile feedback to a user when the plastic snaps are secured. Each of the plastic snaps 60 includes a female plastic snap member 601 and a male plastic snap member 604 configured to be fastened together in a mating engagement. The plastic snaps 60 may be configured for easy alignment and connection and disconnection between the female and male plastic snap members 601, 604. The plastic snaps 60 may also provide audible and tactile feedback indicating that the female and male plastic snap members 601, 604 have been engaged or disengaged from the mating engagement. The plastic snaps 60 may also be configured to have a light weight and a low/flattened profile for comfort and to limit potential skin irritation.

According to an example, the plurality of support members includes at least one support pocket 56, 57 for securing at least one of the plurality of therapy electrodes 11 on the support garment 50, and at least one of the plurality of plastic snaps 60 is disposed on the at least one support pocket 56, 57 and the inside surface of the support garment 50 for releasably securing the at least one support pocket 56, 57 in a closed condition. As shown in FIG. 4A, the support garment 50 includes two plastic snaps 60 for releasably securing the support pocket 56 for the therapy electrodes 11 on the back portion 51 of the support garment 50 and a plastic snap 60 for releasably securing the support pocket 57 on the belt 52 of the support garment 50.

The plurality of support members further includes at least one flap 59 for securing the distribution box 13 on the support garment 50, and at least one of the plastic snaps 60 is disposed on the at least one flap 59 and the inside surface the support garment 50 for releasably securing the flap 59 in a position securing the distribution box 13. As shown in FIG. 4A, the support garment 50 may include three plastic snaps 60 for releasably securing the flap 59 to the inside surface of the support garment 50 in a position securing the distribution box 13 to the support garment 50.

Each of the plurality of plastic snaps 60 includes a male or female plastic snap member 604, 601 disposed on the respective support member and a counterpart female or male plastic snap member 601, 604 disposed on the inside surface of the support garment 50. According to an example, the arrangement of the male and female plastic snap members 604, 601 of the at least one plastic snap 60 for releasably securing the at least one support pocket 56, 57 is reversed from an arrangement of the male and female plastic snap members 604, 601 for releasably securing the at least one flap 59. For example, the plastic snaps 60 for releasably securing the support pockets 56, 57 may each include the male plastic snap member 604 disposed on the inside of the support pocket 56, 57 and the female plastic snap member 601 disposed on the support garment 50, and the plastic snaps 60 for releasably securing the flap 59 may each include the female plastic snap member 601 disposed on the flap 59 and the male plastic snap member 604 disposed on the support garment 50. In this manner, accidental misalignment and fastening of the plastic snap members 601, 604 for releasably securing the flap 59 with the plastic snap members 601, 604 for releasably securing the support pockets 56, 57 can be avoided. It is to be appreciated that the plastic snaps 60 may be provided in any suitable number, arrangement, and spatial configuration for releasably securing the support members, as discussed above.

According to an example, the male and female plastic snap members 604, 601 of each of the plurality of plastic snaps 60 are secured to the respective support member and the inside surface support garment 50 by a color-coded fabric tape 61, 62 indicating the counterpart male and female plastic snap members 604, 601 and the at least one of the plurality of therapy electrodes 11 or the distribution box 13 being secured by the respective support member. According to the example, the fabric tape 61 associated with the support pockets 56, 57 is formed as the handling tab member 61 discussed above with reference to FIGS. 4A, 4B, and 6, which may include a green color corresponding to colored indicators provided on the therapy electrodes 11 and the support pockets 56, 57. As also discussed above, corresponding pieces of fabric tape (not shown) may be provided on the support garment 50 for securing the counterpart male or female plastic snap member 604, 601 for the male or female plastic snap member 604, 601 disposed on the handling tab member 61.

The pieces of fabric tape 62 associated with the plastic snaps 60 for releasably securing the flap 59 may be affixed, such as by sewing, to the interior surfaces of the flap 59 and the support garment 50. According to an example, the pieces of fabric tape 62 on the flap 59 and the support garment 50 are color coded with a corresponding blue color. The distribution box 13 may include a blue-colored indicator corresponding to the blue color of the pieces of fabric tape 62 for releasably securing the flap 59. The pieces of fabric tape 62 on the flap 59 and the support garment 50 may be formed from the same cotton twill material as the handling tab members 61.

According to an example, each of the pieces of fabric tape 62 on the flap 59 and the support garment 50 has a width of approximately 0.5"-1.5", more particularly approximately 1.0", and a length of approximately 2"-4", more particularly approximately 2.5"-3.5", more particularly approximately 3.0". The pieces of fabric tape provided on the interior surface of the support garment 50 opposite to the handling tab members 61 may be of the same size and configuration as the pieces of fabric tape 62 on the flap 59 and the support garment 50. It is to be appreciated that the pieces of fabric tape 62 may be of any suitable length and width.

As shown in FIGS. 9A and 9B, each plastic snap 60 includes the female plastic snap member 601 and the male plastic snap member 604 configured to form a mating engagement with each other. Each female plastic snap member 601 includes a cap 602 and a socket 603. The cap 602 includes a portion configured to pass through the respective piece of fabric tape 61, 62 to engage the socket 603 disposed on an opposite side of the respective piece of fabric tape 61, 62 to fasten the socket 603 on the respective piece of fabric tape 61, 62. Each male plastic snap member 604 includes a post 605 and a stud 606. The post 605 includes a portion configured to pass through the respective piece of fabric tape 61, 62 to engage the stud 606 disposed on an opposite side of the respective piece of fabric tape 61, 62 to fasten the stud 606 on the respective piece of fabric tape 61, 62. According to an example, the cap 602 of the female plastic snap member 601 and the post 605 of the male plastic snap member 604 are disposed between layers of the respective piece of fabric tape 61, 62 or between the respective piece of fabric tape 61, 62 and the interior surface of the support garment 50.

The stud 606 of the male plastic snap member 604 includes a protruding portion configured to be received in and engage a recess formed in the socket 603 of the female plastic snap member 603 to form the mating engagement between the male and female plastic snap members 604, 601. The stud 606 is pulled or withdrawn from the socket 603 to disconnect the male and female plastic snap members 604, 601. The engagement or disengagement of the stud 606 of the male plastic snap member 604 with the socket 603 of the female plastic snap member 601 creates the audible and tactile feedback indicating that the plastic snap 60 has been closed or opened.

According to an example, the cap 602 of the female plastic snap member 601 defines a maximum outer diameter C of each of the plurality of plastic snaps 60. Each of the plurality of plastic snaps 60 may have a maximum diameter C of approximately 10 mm-20 mm, more particularly approximately 14-16 mm, more particularly approximately 14.5 mm-15.5 mm, more particularly 14.7 mm.

According to an example, the plurality of plastic snaps 60 are comprised of polyacetal. It is to be appreciated that the plastic snaps 60 may be of any suitable construction, structure, size, and material and may be arranged on the support garment 50 in any suitable manner.

According to an example, each of the plurality of plastic snaps has a medium standard snap force, or a force required to fasten and/or unfasten each of the plurality of plastic snaps of approximately 1 lbf-4 lbf, more particularly 1.5 lbf-3 lbf, and more particularly 1.75 lbf-2.5 lbf.

According to the example, the plurality of plastic snaps 60 are structured, as discussed above with reference to FIGS. 9A and 9B, to have a snap tension or tensile force required to pull apart or unfasten the plastic snap 60 that is sufficiently large enough to maintain closure of the of the support pockets 56, 57 and the flap 59 on the support garment 50 against the weight and size of the therapy electrodes 11 and the distribution box 13 and against the stresses, strains, and forces applied to the support garment during normal use and sufficiently small enough that the plastic snaps 60 can be conveniently unfastened to open the support pockets 56, 57 or the flap 59. The plurality of plastic snaps 60 may additionally be structured to maintain a desirable snap tension over the extended period of time that the support garment 50 may be in use and over multiple use cycles (fastening and unfastening) of the plastic snaps 60 and through multiple wash cycles of the support garment 50.

Figure 10:
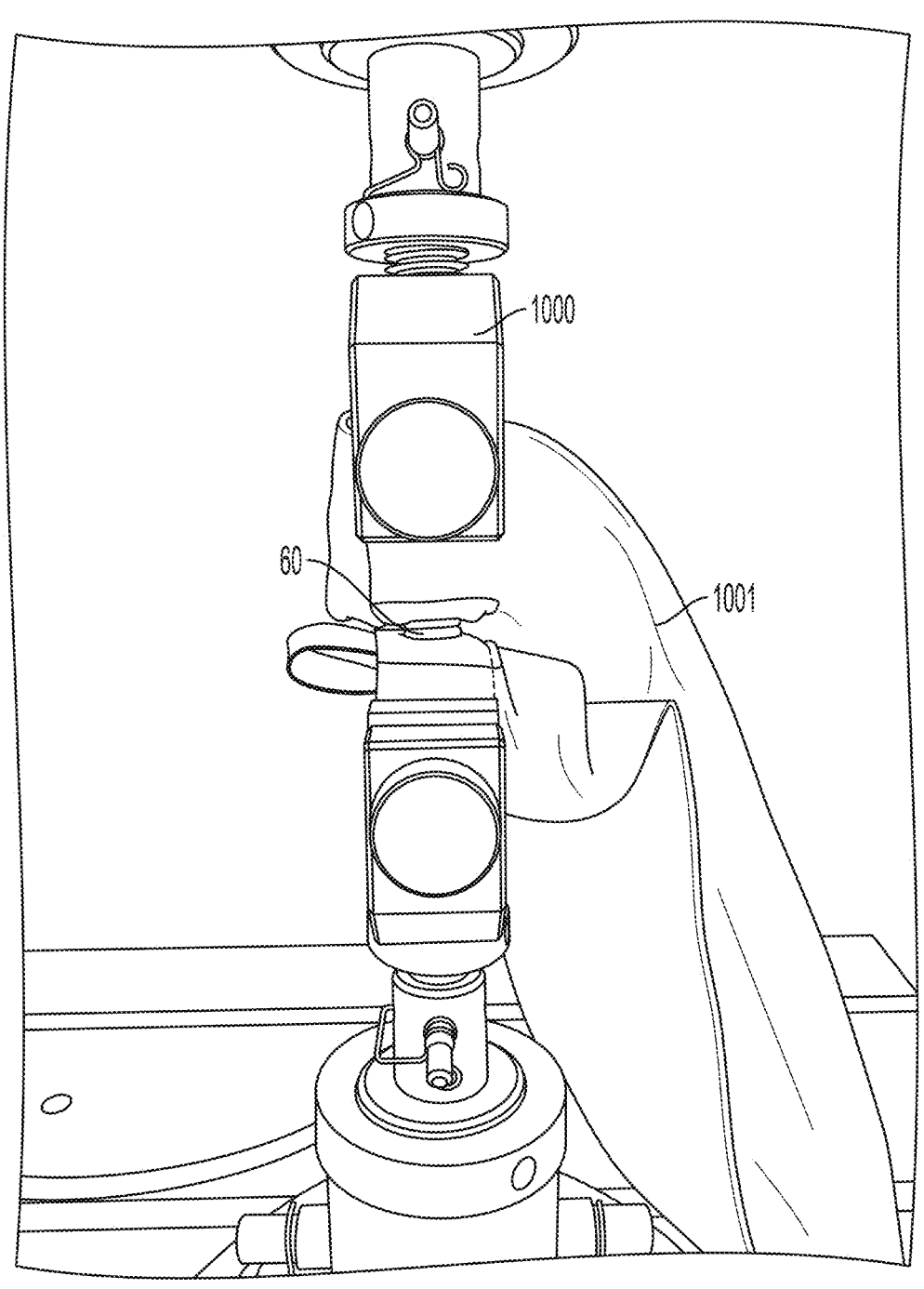
FIG. 10 is a front view of a testing device and setup for measuring a tensile force required to separate the male and female plastic snap members of the plastic snap of FIG. 8.

FIG. 10 illustrates an exemplary testing device 1000 and setup for measuring the snap tension/tensile force of the plastic snaps 60. The testing device 1000 is a Universal Testing System for tensile strength testing manufactured by INSTRON®. The testing device 1000 was arranged and configured to pull apart or unfasten a plastic snap 60 disposed on a sample test swatch 1001 at a constant strain rate until the male and female plastic snap members 604, 601 disengage from each other and to measure the maximum tensile force applied to the plastic snap 60 while being pulled apart before disengaging. Testing was performed on multiple samples of the plastic snaps 60.

Figure 11A:
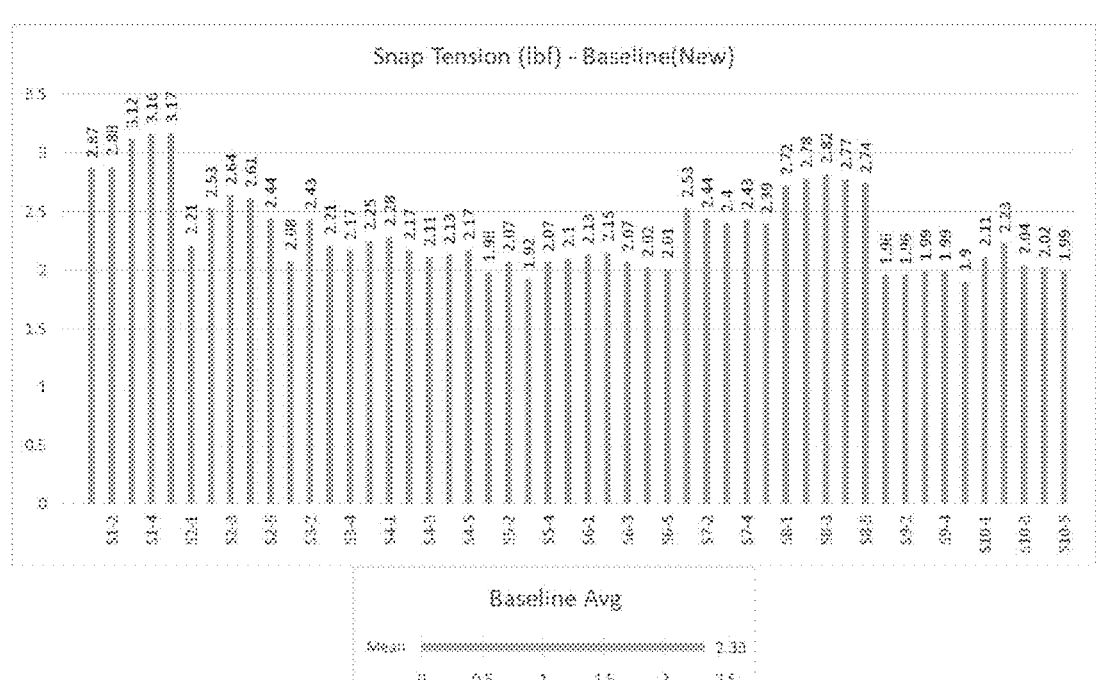
FIGS. 11A-11D are charts illustrating the testing results for measuring the tensile force required to separate the male and female snap members of a number of samples of the plastic snap of FIG. 8 when new (baseline) (FIG. 11A), after 180 cycles of use (FIG. 11B), after 360 cycles of use (FIG. 11C), and after 540 cycles of use (FIG. 11D).

FIGS. 11A-11D illustrate the testing results for the snap tension or tensile force measured by the testing device 1000 to pull apart or unfasten samples of the plastic snaps 60 over multiple cycles of use, i.e., fastening and unfastening, to assess the durability of the plastic snaps 60 over multiple cycles of use. FIG. 11A illustrates the measured snap tension or tensile force required for unfastening the sample plastic snaps 60 when the plastic snaps 60 are new and have undergone zero or very few cycles of use. As shown, ten new plastic snap samples were fastened and unfastened 5 times each. The plastic snap samples exhibited a snap tension ranging between 1.9 lbf and 3.17 lbf when new. The average snap tension of the new sample plastic snap samples over the five cycles was 2.33 lbf.

Figure 11B:
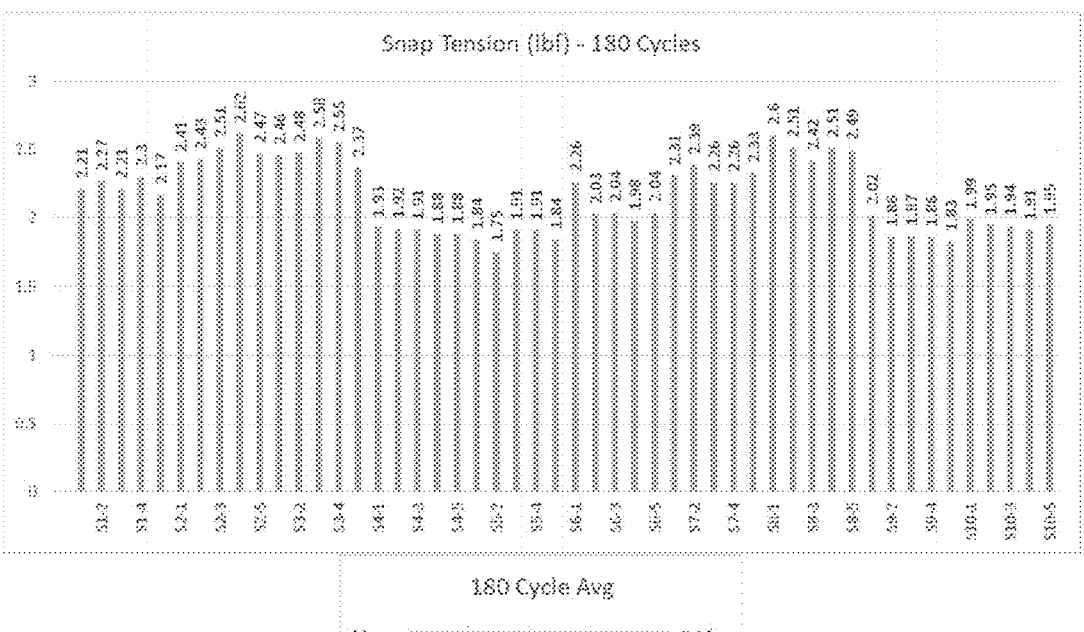

FIG. 11B illustrates the measured snap tension of the ten plastic snap samples after having undergone 180 cycles of use. As shown, the plastic snap samples were fastened and unfastened five times each after having undergone 180 cycles of use. The plastic snap samples exhibited a snap tension ranging between 1.75 lbf and 2.62 lbf after 180 cycles of use. The average snap tension of the plastic snap samples over the five cycles was 2.17 lbf.

Figure 11C:
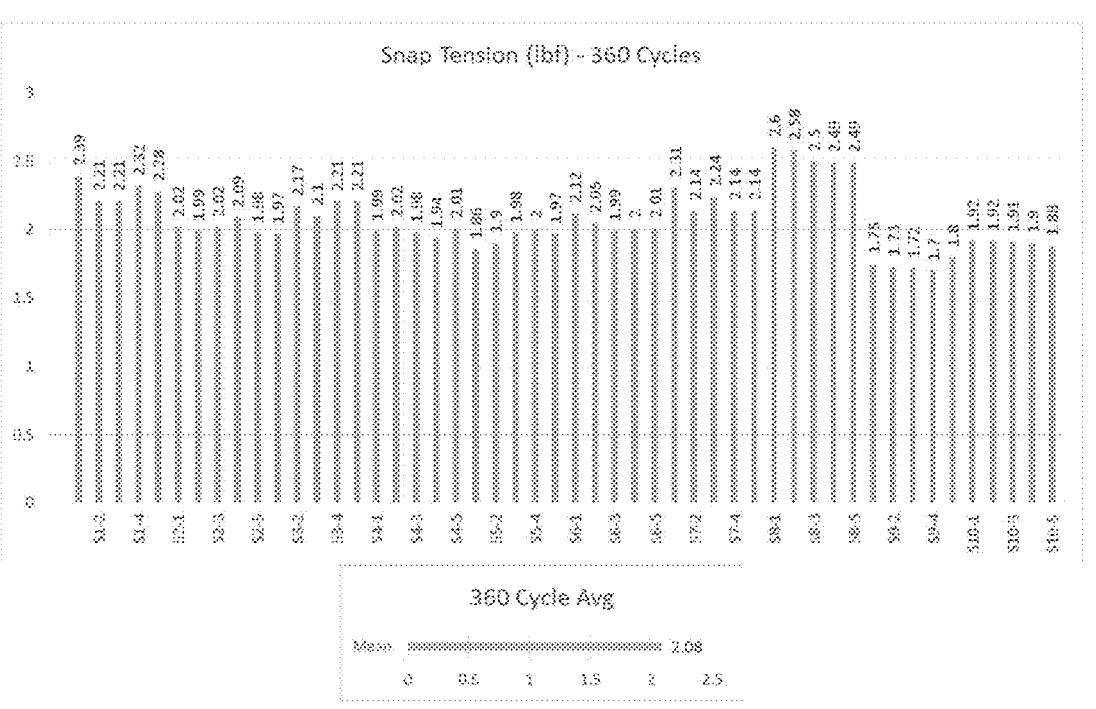

FIG. 11C illustrates the measured snap tension of the ten plastic snap samples after having undergone 360 cycles of use. As shown, the plastic snap samples were fastened and unfastened five times each after having undergone 360 cycles of use. The plastic snap samples exhibited a snap tension ranging between 1.7 lbf and 2.6 lbf after 360 cycles of use. The average snap tension of the plastic snap samples over the five cycles was 2.08 lbf.

Figure 11D:
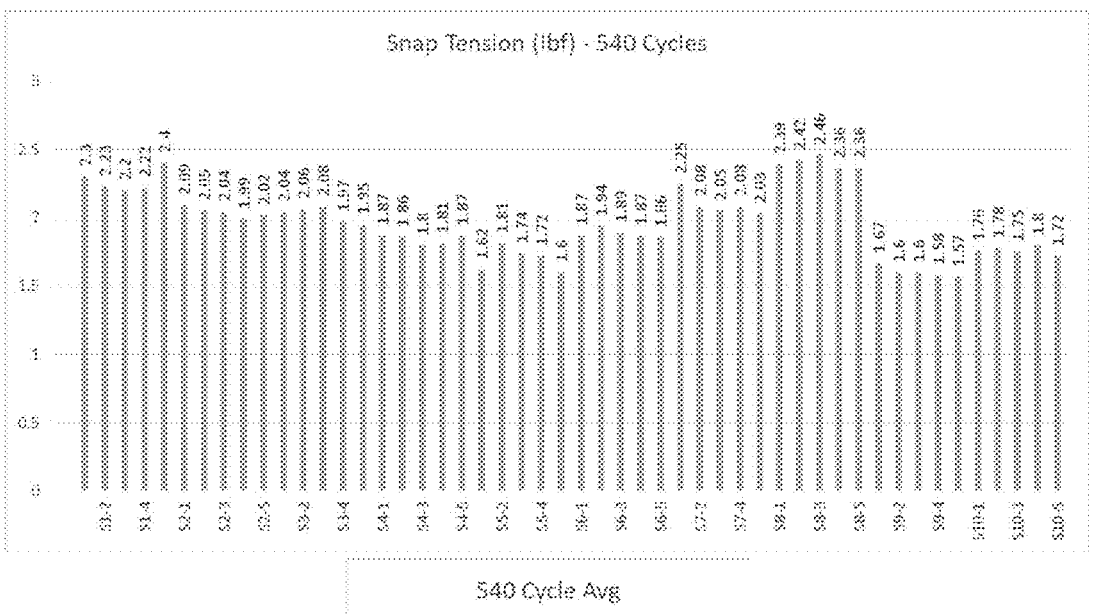
Figure 12A:
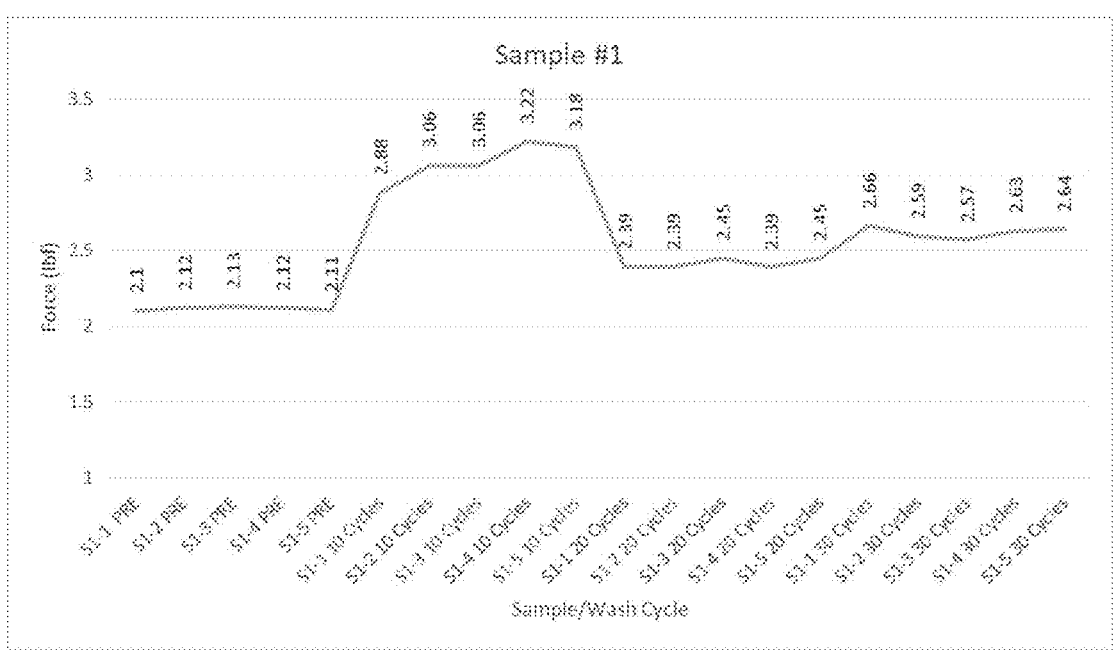
FIGS. 12A-12D are charts illustrating the testing results for measuring the tensile force required to separate the male and female plastic snap members of first (FIG. 12A), second (FIG. 12B), third (FIG. 12C), and fourth (12D) samples of the plastic snap of FIG. 8 after being exposed to 0, 10, 20, and 30 wash cycles.
Figure 12B:
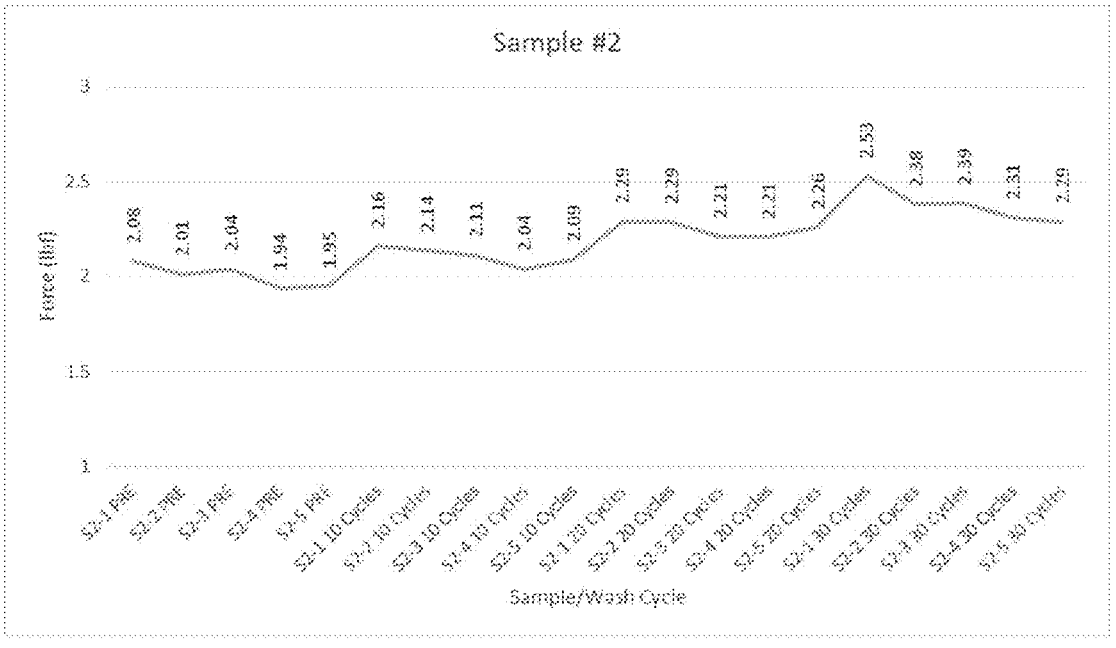
Figure 12C:
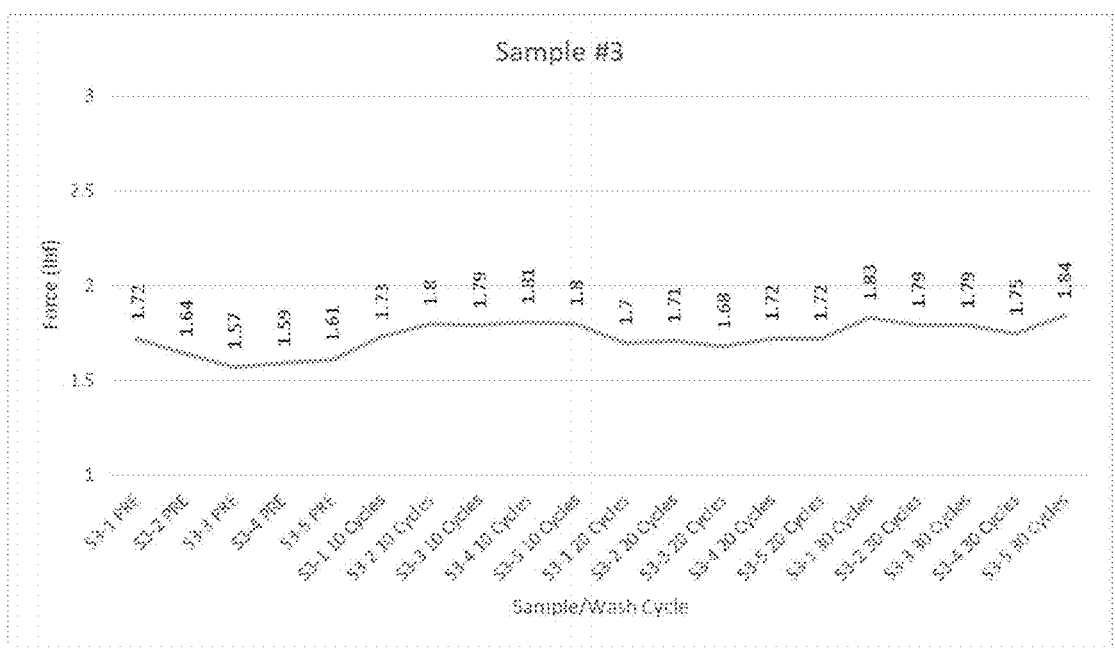
Figure 12D:
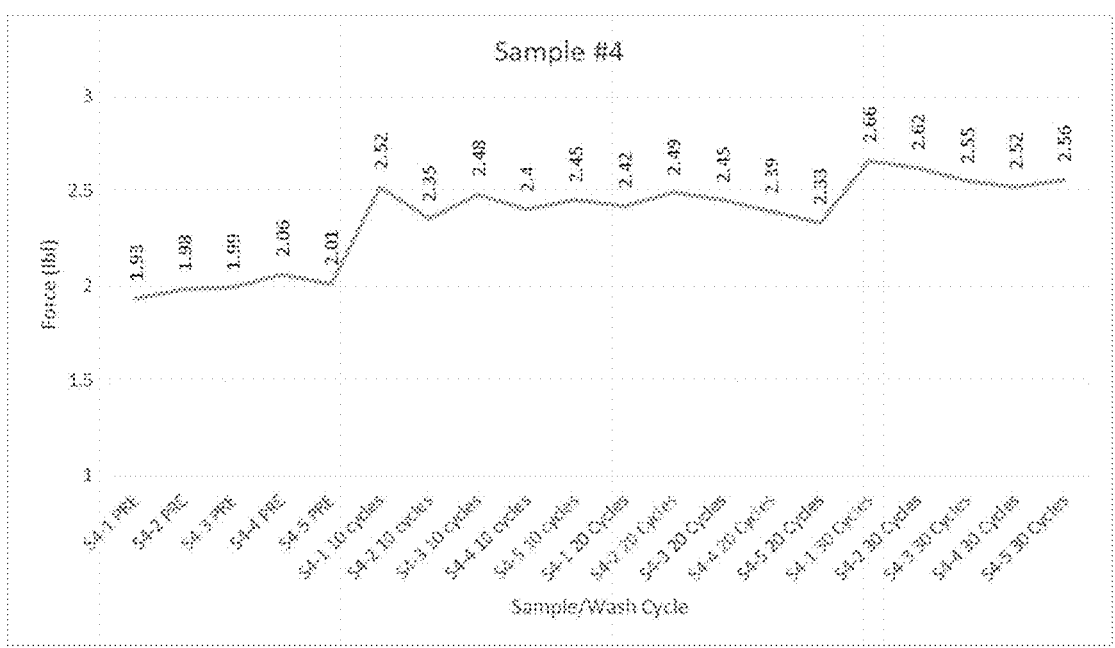

FIG. 11D illustrates the measured snap tension of the ten plastic snap samples after having undergone 540 cycles of use. As shown, the plastic snap samples were fastened and unfastened five times each after having undergone 540 cycles of use. The plastic snap samples exhibited a snap tension ranging between 1.57 lbf and 2.46 lbf after 540 cycles of use. The average snap tension of the plastic snap samples over the five cycles was 1.96 lbf.

As can be appreciated from results illustrated in FIGS. 11A-11D, the plastic snap samples exhibited a consistent snap tension remaining within a suitable range through multiple cycles of fastening and unfastening. In particular, the snap tension of the plastic snap samples remained above approximately 1.5 lbf.

Testing on the plastic snap samples was also performed to assess the durability of the plastic snaps 60 over multiple garment washing cycles. FIGS. 12A-12D illustrate the testing results for the snap tension or tensile force measured by the testing device 1000 to pull apart or unfasten four plastic snap samples over multiple garment washing cycles. The snap tension of each plastic snap sample was measured for five cycles of use prior to washing, for five cycles of use after having undergone 10 wash cycles, for five cycles of use after having undergone 20 wash cycles, and for five cycles of use after having undergone 30 wash cycles. For reference, patients may be instructed to wash their support garments every day or nearly every day. Accordingly, 30 wash cycles represents an approximate typical number of wash cycles of the support garment for a month. As shown in FIGS. 12A-12D, exposure to multiple wash cycles did not negatively affect the snap tension of the sample plastic snaps in an appreciable manner. The plastic snap samples exhibited a consistent snap tension remaining within a suitable range through multiple wash cycles. In particular, the snap tension of the plastic snap samples remained above approximately 1.5 lbf.

With reference to FIG. 4A, according to an example of the present disclosure, the support garment 50 may be incorporated into a wearable cardiac therapeutic device with improved aesthetic features.

The device includes a plurality of ECG sensing electrodes 12 configured to sense ECG signals regarding a cardiac function of a patient, a plurality of therapy electrodes 11 configured to deliver transcutaneous defibrillation shocks or transcutaneous pacing pulses to the patient's heart, and a support garment 50 configured to support and hold the plurality of ECG sensing electrodes 12 and the plurality of therapy electrodes 11 against the patient's body.

The support garment 50 includes a fabric material F having a gray color configured to have a neutral and appealing aesthetic appearance. The gray color of the fabric material F of the support garment 50 offers an appearance that is neutral for both men and women and that may not stand out under certain clothing. Additionally, the gray color may be incorporated into the support garment 50 to provide the support garment 50 with a more modern and stylized appearance typically associated with sportswear, activewear, and fitted athletic clothing.

According to an example, the gray color of the fabric material F is PANTONE 16-3850 TPX (Silver Sconce). It is to be appreciated that the gray color may be of any suitable gray color variation or value. It is also to be appreciated that other elements of the support garment 50, for instance the bias tape forming the trim for the ends 66, 67 of the belt and the openings of the support pockets 56, 57 may also be colored gray to correspond to the gray color of the fabric material F.

According to an example, the fabric material F of the support garment has an anti-microbial treatment applied thereto. The anti-microbial treatment may include a polymer application configured to deliver silver ions.

According to an example, the fabric material F includes a tricot fabric, the tricot fabric including nylon and spandex materials. The tricot fabric may include approximately 65%-90% nylon material, more particularly 70%-85% nylon material, more particularly 77% nylon material. According to an example, the remainder of the fabric material F with the above-listed percentages of nylon material is comprised of spandex material. It is to be appreciated that the fabric material F chosen for the support garment 50 may be comprised of any suitable materials or combinations of materials.

With reference to FIG. 4A, according to an example of the present disclosure, the support garment 50 may be incorporated into a wearable cardiac therapeutic device having improved hygiene, cleanliness and wearability.

The device includes a plurality of ECG sensing electrodes 12 configured to sense ECG signals regarding a cardiac function of a patient, a plurality of therapy electrodes 11 configured to deliver transcutaneous defibrillation shocks or transcutaneous pacing pulses to the patient's heart, and a support garment 50 configured to support and hold the plurality of ECG sensing electrodes 12 and the plurality of therapy electrodes 11 against the patient's body.

The support garment 50 includes a fabric material F having an anti-microbial treatment applied thereto. The anti-microbial treatment is configured to limit or prevent odor and bacterial growth on the support garment 50. The patient may be required to wear the support garment 50 continuously or nearly continuously for an extended period of time. The support garment 50 must be worn directly against the patient's skin. Accordingly, the support garment 50 may take on bacterial growth and odor over the course of continuous wear between washes or over time, even with frequent washing. Bacterial growth may also cause staining and discoloration of the fabric material F and lead to reduction in textile mechanical strength. Additionally, some patients may have improper hygiene and may not launder or change the support garment 50 according to instructions. The application of the anti-microbial treatment alleviates the development of odor and bacterial growth on the support garment 50 to improve the durability, cleanliness, and wearability of the support garment 50.

According to an example, the anti-microbial treatment comprises a polymer application configured to deliver silver ions. The anti-microbial treatment may be configured to deliver low levels of silver ions in response to the presence or absorption of a micro-organism, such as a bacteria, on the support garment 50. The silver ions emitted by the treatment neutralize the micro-organism by binding to the micro-organism's DNA to prevent replication, causing changes to the cellular membrane so that it cannot function properly. The treatment may also be configured to block absorption of odorants and to target enzymes to prevent production of odors. The treatment may also be configured to be non-irritating to the patient's skin. The treatment may form an insoluble polymer network on the surface of the fabric material F, which allows for a highly durable antimicrobial action to control micro-organism growth and buildup.

According to an example, the anti-microbial treatment is comprised of the SILVADUR™ 930 treatment manufactured by DuPont. It is to be appreciated that the anti-microbial treatment applied to the support garment 50 may be of any suitable type.

According to an example, the fabric material F of the support garment 50 has a neutral, gray color.

According to an example, the fabric material F includes a tricot fabric, the tricot fabric including nylon and spandex materials. The tricot fabric may include approximately 65%-90% nylon material, more particularly 70%-85% nylon material, more particularly 77% nylon material. The fabric material F may be configured to wick moisture away from the patient's skin. It is to be appreciated that the fabric material F chosen for the support garment 50 may be comprised of any suitable materials or combinations of materials.

With reference to FIGS. 4A-8, 13, and 15, according to an example of the present disclosure, the support garment 50 may be incorporated into a wearable cardiac therapeutic device with improved aesthetic and comfort features.

The device includes a plurality of ECG sensing electrodes 12 configured to sense ECG signals regarding a cardiac function of a patient, a plurality of therapy electrodes 11 configured to deliver transcutaneous defibrillation shocks or transcutaneous pacing pulses to the patient's heart, and a support garment 50 configured to support and hold the plurality of ECG sensing electrode 12 and the plurality of therapy electrodes 11 against the patient's body.

The support garment 50 includes an aesthetic edge binding 63 surrounding at least a portion of a periphery of the support garment 50. According to an example, the aesthetic edge binding 63 may completely surround the periphery of the support garment 50, as shown in FIG. 4A. The aesthetic edge binding 63 includes nylon and spandex materials and is configured to have an appealing aesthetic appearance and comfortable feel to the patient. The aesthetic edge binding 63 may be configured to provide improved comfort to the patient by having a softened hand feel and by limiting or avoiding digging into the skin and rubbing on the skin in an irritating manner. Additionally, the aesthetic edge binding 63 may be incorporated into the support garment 50 to provide the support garment 50 with a more modern and stylized appearance typically associated with sportswear, activewear, and fitted athletic clothing.

According to an example, the aesthetic edge binding 63 is formed in a V-fold configuration, which is provided as a strip and folded over the raw edges of the support garment 50 and then machine stitched to the interior and exterior surfaces of the support garment 50. It is to be appreciated that the edge binding 63 may be of any suitable configuration and affixed to the support garment 50 in any suitable manner.

According to an example, the aesthetic edge binding 63 has an unfolded width of approximately 12 mm-20 mm, more particularly approximately 14 mm-18 mm, more particularly approximately 15 mm-17 mm, more particularly approximately 16 mm. According to another example, the edge binding 63 has a thickness of approximately 0.4 mm-1.2 mm, more particularly approximately 0.6 mm-1.0 mm, more particularly approximately 0.75 mm-0.85 mm, more particularly approximately 0.8 mm. It is to be appreciated that the aesthetic edge binding 63 may be provided in any suitable size.

According to an example, the aesthetic edge binding includes approximately 85%-95% nylon material, more particularly approximately 88%-94% nylon material, more particularly approximately 91% nylon material. It is to be appreciated that the aesthetic edge binding 63 may include any suitable material or combination of materials.

According to an example, the aesthetic edge binding 63 has a color complementary to a color of a fabric material F of the support garment 50. For instance, the color of the edge binding 63 may be PANTONE 14-4203 TPG (Vapor Blue), which is a suitable complement for the gray color of the support garment 50, as discussed above. It is to be appreciated that the aesthetic edge binding 63 may be provided in any suitable color.

Figure 13:
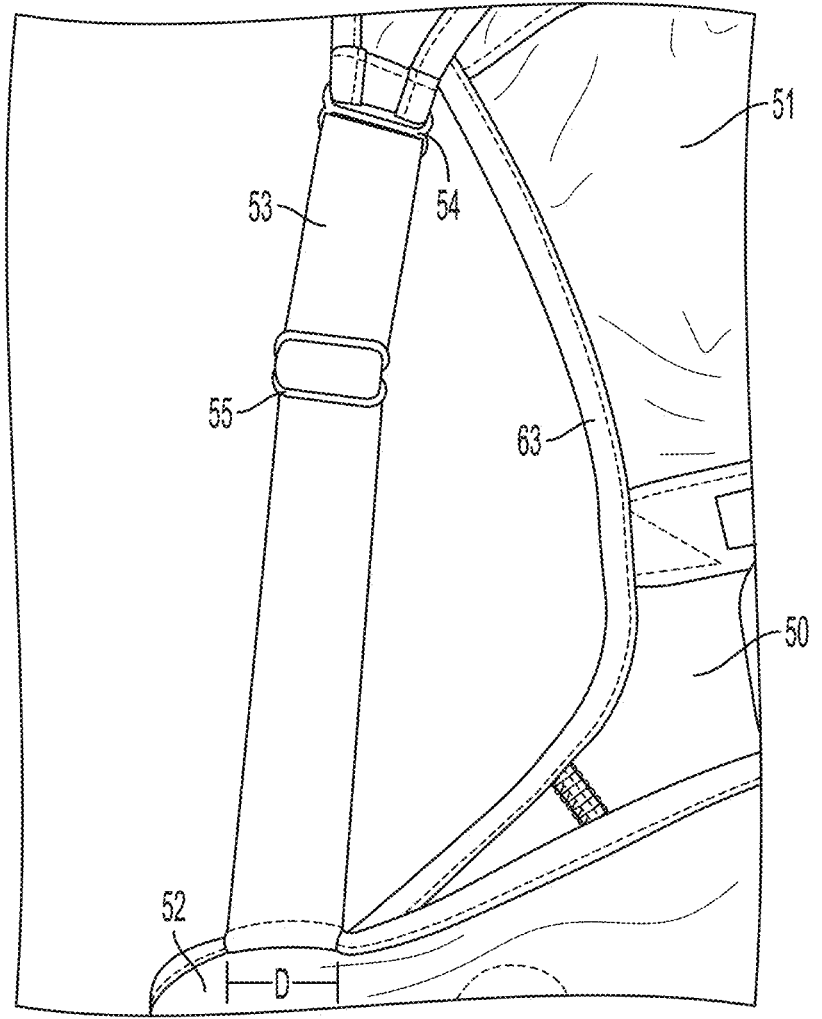
FIG. 13 is an enlarged view of a shoulder strap and strap slides of the support garment of FIGS. 4A and 4B that may be used in connection with the present disclosure.

With reference to FIGS. 4A, 4B, and 13, according to an example of the present disclosure, the support garment 50 may be incorporated into a wearable cardiac therapeutic device with improved comfort features.

The device includes a plurality of ECG sensing electrodes 12 configured to sense ECG signals regarding a cardiac function of a patient, a plurality of therapy electrodes 11 configured to deliver transcutaneous defibrillation shocks or transcutaneous pacing pulses to the patient's heart, and a support garment 50 configured to support and hold the plurality of ECG sensing electrodes 12 and the plurality of therapy electrodes 11 against the patient's body.

The support garment 50 includes a back portion 51, a belt 52 defined by side portions extending from the back portion 51 and around a front of the patient's torso, and at least one shoulder strap 53 extending between the back portion 51 and the belt 52. According to an example, the support garment 50 may include two shoulder straps 53 extending between the back portion 51 and the belt 52 on the left and right sides of the support garment, as shown in FIG. 4A.

The shoulder strap(s) 53 includes a double plush elastic material, which is configured to have a comfortable feel to the patient. The shoulder strap(s) 53 may be configured to provide improved comfort to the patient by having a softened hand feel and by limiting or avoiding digging into the skin and rubbing on the skin in an irritating manner.

According to an example, the shoulder strap(s) has a width D of approximately 0.5"-1.5", more particularly approximately 0.75"-1.25", more particularly approximately 0.9"-1.1", more particularly approximately 1.0". It is to be appreciated that the shoulder strap(s) 53 may be provided with any suitable width.

According to an example, the double plush elastic material of the shoulder strap(s) 53 includes polyester, spandex, and nylon materials. The double plush elastic material of the shoulder strap(s) may have an elastic elongation of 125%-200%, more particularly 140%-160%, more particularly 150%. It is to be appreciated that the shoulder strap(s) 53 may include any suitable material or combination of materials and may have any suitable elastic elongation.

According to an example, the double plush elastic material of the shoulder strap(s) 53 has a color complementary to a color of a fabric material F of the support garment 50. For instance, the double plush elastic material may be provided with a gray color that is complementary to the gray color of the support garment 50, as discussed above. It is to be appreciated that the shoulder strap(s) 53 may be provided in any suitable color.

With reference to FIGS. 4A, 4B, and 13-14B, according to an example of the present disclosure, the support garment 50 may be incorporated into a wearable cardiac therapeutic device with improved features for comfort and wearability.

The device includes a plurality of ECG sensing electrodes 12 configured to sense ECG signals regarding a cardiac function of a patient, a plurality of therapy electrodes 11 configured to deliver transcutaneous defibrillation shocks or transcutaneous pacing pulses to the patient's heart, and a support garment 50 configured to support and hold the plurality of ECG sensing electrodes 12 and the plurality of therapy electrodes 11 against the patient's body.

The support garment includes a back portion 51, a belt 52 defined by side portions extending from the back portion 51 and around a front of the patient's torso, and at least one shoulder strap 53 extending between the back portion 51 and the belt 52.

The support garment 50 further includes at least one first strap slide 54 configured to attach the shoulder strap 53 to the back portion 51 and at least one second strap slide 55 configured to provide length adjustment to the shoulder strap 53. The at least one first strap slide 54 and the at least one second strap slide 55 each comprise a coated metal material and are configured to have a low profile, provide high coverage of the shoulder strap 53 and a comfortable feel to feel to the patient, and facilitate physical manipulation and length adjustment of the shoulder strap 53. The at least one first strap slide 54 and the at least one second strap slide 55 may be sized and configured with respect to the shoulder strap 53 to facilitate sliding of the shoulder strap 53 within the first strap slide 54 and the second strap slide 55 so that the patient may more easily tighten the shoulder strap 53 to properly secure the support garment 50 to the patient's body. The first strap slide 54 and the second strap slide 55 may further incorporate a low friction coating thereon to further facilitate sliding of the shoulder strap 53 with respect to the first and second strap slides 54, 55. The first strap slide 54 and the second strap slide 55 may be configured to provide improved comfort to the patient by limiting or avoiding digging into the skin and rubbing on the skin in an irritating manner. Either or both of the first strap slide 54 and the second strap slide 55 may include features to facilitate grasping and handling by the patient.

According to an example, the support garment 50 may include two shoulder straps 53 extending between the back portion 51 and the belt 52 on the left and right sides of the support garment, as shown in FIG. 4A. Each shoulder strap 53 is attached to the back portion 51 of the support garment 50 by a respective first strap slide 54 and includes a respective second strap slide 55 positioned thereon to provide for length adjustment of the shoulder strap 53. The shoulder straps 53 may be affixed to the respective side portions of the belt 52 by stitching.

According to an example, the at least one first strap slide 54 and the at least one second strap slide 55 comprise a steel material with a nylon coating applied thereto. It is to be appreciated that the first strap slide 54 and the second strap slide 55 may be comprised of any suitable material or combination of materials and may be provided with any suitable coatings or no coating at all.

According to an example, the first strap slide 54 and the second strap slide 55 have a color complementary to a color of a fabric of the support garment. For instance, the color of the first strap slide 54 and the second strap slide 55 may be PANTONE 14-4203 TPG (Vapor Blue), which is a suitable complement for the gray color of the support garment 50, as discussed above. It is to be appreciated that the first strap slide 54 and the second strap slide 55 may be provided in any suitable color.

Figure 14A:
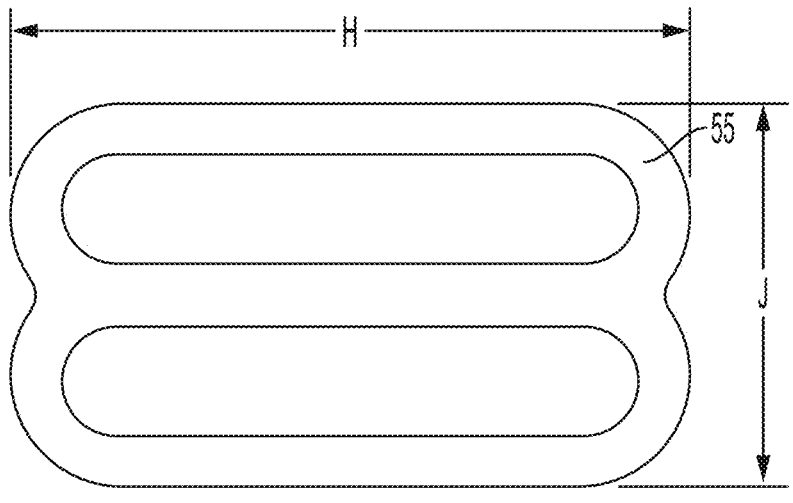
FIG. 14A is a front view of a second strap slide of the support garment of FIGS. 4A and 4B that may be used in connection with the present disclosure.
Figure 14B:
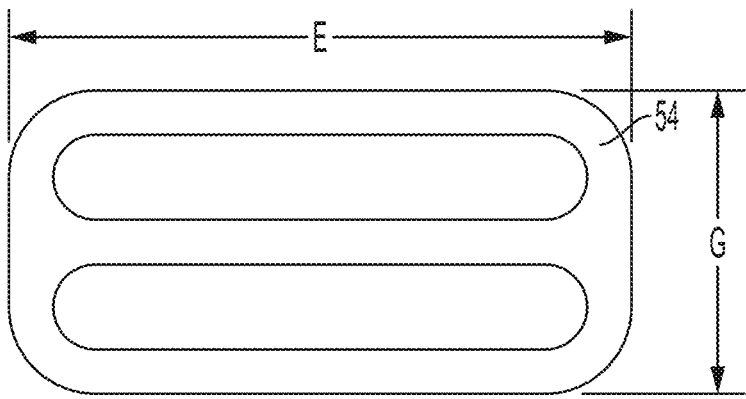
FIG. 14B is a front view of a first strap slide of the support garment of FIGS. 4A and 4B that may be used in connection with the present disclosure.

According to an example, as shown in FIG. 14B, the at least one first strap slide 54 includes straight sides. The at least one first strap slide may have a width E of approximately 25 mm-35 mm, more particularly approximately 28 mm-30 mm, more particularly approximately 28.8 mm. The at least one first strap slide 54 may have a height G of approximately 10 mm-20 mm, more particularly approximately 13 mm-14 mm, more particularly approximately 13.6 mm. The at least one first strap slide may have a thickness of approximately 1 mm-2 mm, more particularly approximately 1.1 mm-1.7 mm, more particularly approximately 1.4 mm.

According to an example, as shown in FIG. 14A, the at least one second strap slide 55 includes indented sides, which may be configured to facilitate handling and grasping of the second strap slide 55 to allow for easier sizing of the shoulder strap 53. The at least one second strap slide 55 may have a width H of approximately 25 mm-35 mm, more particularly approximately 28 mm-30 mm, more particularly approximately 28.8 mm. The at least one second strap slide 55 may have a height J of approximately 10 mm-20 mm, more particularly approximately 15 mm-17 mm, more particularly approximately 16.1 mm. The at least one second strap slide 55 may have a thickness of approximately 1 mm-2 mm, more particularly approximately 1.0 mm-1.6 mm, more particularly 1.3 mm.

It is to be appreciated that the first strap slide 54 and the second strap slide 55 may be of any suitable shape or configuration. Additionally, the first strap slide 54 and the second strap slide 55 may not be provided in different shapes. Rather, both strap slides 54, 55 may have the indented configuration shown in FIG. 14A or the straight configuration shown in FIG. 14B or the configuration of the strap slides 54, 55 with the straight strap slide being provided to adjust the sizing of the shoulder strap 53 and the indented strap slide being provided to connect the shoulder strap 53 to the back portion 51 of the support garment 50. It is also to be appreciated that the strap slides 54, 55 may have any suitable length, height, and thickness dimensions.

With reference to FIGS. 4A, 4B and 15-18, according to an example of the present disclosure, the support garment 50 may be incorporated into a wearable cardiac therapeutic device with an improved mechanism for securing the device on the body of a patient.

The device includes a plurality of ECG sensing electrodes 12 configured to sense ECG signals regarding a cardiac function of a patient, a plurality of therapy electrodes 11 to deliver transcutaneous defibrillation shocks or transcutaneous pacing pulses to the patient's heart, and a support garment 50 configured to support and hold the plurality of ECG sensing electrodes 12 and the plurality of therapy 11 electrodes against the patient's body.

The support garment 50 includes a back portion 51, a belt 52 defined by side portions extending from the back portion 51 and around a front of the patient's torso, and a closure mechanism 65 configured to connect the side portions at the front of the patient's torso.

The closure mechanism 65 includes a first clasp member 68 disposed on one of the side portions forming the belt 52 and a second clasp member disposed on another of the side portions forming the belt 52. The first clasp member 68 and the second clasp member 69 are identical. The first clasp member 68 and the second clasp member 69 are configured to form a mating engagement with each other to secure the side portions forming the belt 52. The first and second clasp members 68, 69 are configured to facilitate mutual alignment and securing of the side portions at the front of the patient, provide tactile feedback to a user that the clasp members 68, 69 are matingly engaged, and have an appealing aesthetic appearance. The first and second clasp members 68, 69 may also be configured to have a low profile so as to not protrude extensively from the support garment 50 and to limit visibility under the patient's clothing. The first and second clasp members 68, 69 may also include visual features indicating that the clasp members 68, 69 are properly positioned with respect to each other to form the mating engagement.

Figure 16:
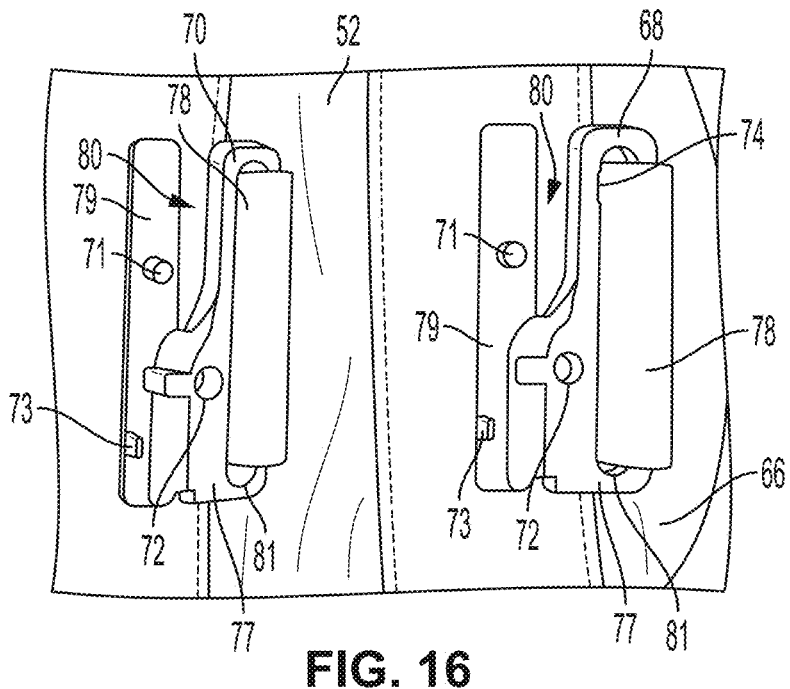
FIG. 16 is an enlarged view of one side of the closure mechanism of FIG. 15.

According to an example, as shown in FIG. 16, the closure mechanism 65 further includes a third clasp member 70 disposed on the same side portion as the first clasp member 68 at a different location along a length of the side portion. The third clasp member 70 is identical to the first clasp member 68 and the second clasp member 69 and is configured to form a mating with the second clasp member 69 to secure the side portions of the belt 52. Accordingly, the length of the belt 52 may be adjusted by connecting the second clasp member 69 with the first clasp member 68 positioned closer to the end 66 of the side portion, thus lengthening the belt 52, or by connecting the second clasp member 69 with the third clasp member 70 positioned farther from the end 66 of the side portion, thus shortening the belt 52, in order to provide a more customized fit to the patient.

Figure 18:
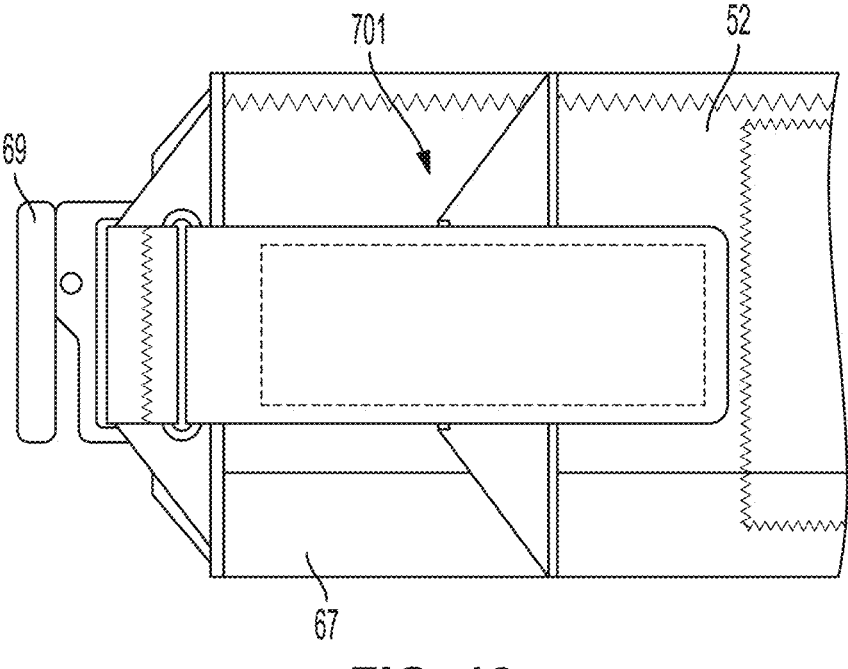
FIG. 18 is an enlarged view of a belt attachment and adjustable slider for connecting a clasp member of the closure mechanism of FIG. 15 to the belt that may be used in connection with the present disclosure.

It is to be appreciated that any suitable mechanism or configuration of the clasp members 68, 69, 70 may be utilized to provide for adjustability to the size of the belt. For instance, as shown in FIG. 18, the second clasp member 69 may be connected to the end 67 of the respective side portion of the belt 52 by a belt attachment and adjustable slider 701 that provides for an adjustable sizing of the belt 52 by adjusting the position of the second clasp member 69 on the end 67 of the respective side portion. The belt attachment and adjustable slider 701 may be manipulated to move the second clasp member 69 inwardly or outwardly along the respective side portion of the belt 52 to effectively change the size of the belt 52 on the patient and provide for a more customized fit to the patient. According to an alternative example, the first clasp member 68 may be connected to the end 66 of the other side portion of the belt 52.

As shown in FIGS. 15-17D, each clasp member 68, 69, 70 includes a recessed portion 77 that defines a closed slot 81 that receives a fabric loop 78 stitched to the respective side portion of the belt 52 to fasten the clasp member 68, 69, 70 to the belt 52. Each clasp member 68, 69, 70 also includes a locking portion 79 disposed over the recessed portion 77 and extending away from the recessed portion 77. An open-ended slot 80 is defined between the locking portion 79 and the recessed portion 77. The first clasp member 68 (and third clasp member 70) and the second clasp member 69 are oriented opposite to each other so that the open-ended slots 80 are open in opposing directions.

The clasp members 68, 69, 70 also include corresponding protrusion and recess features 71-74 configured to indicate proper alignment of the clasp members 68, 69, 70 to form the mating engagement, as will be discussed below, and to engage each other to secure the clasp members 68, 69, 70 in the mating engagement. The protrusion and recess features 71-74 are also configured to snap together to provide audible and tactile feedback to the user that the clasp members 68, 69, 70 have been secured in the mating engagement to close the belt 52 or have been disengaged to open the belt 52.

According to an example, the corresponding protrusion and recess features 71-74 include a post 71 disposed on an inside surface of the locking portion 79 and a corresponding hole 72 defined in the recessed portion 77, and a hook 73 disposed on an outer side of the locking portion 79 and a corresponding notch 74 defined in the recessed portion 77 at the closed slot 81.

According to an example, the clasp members 68, 69, 70 also each include at least one smooth-textured protrusion 75 disposed on a rough-textured exterior surface 76 of the locking portion 79. The smooth-textured protrusions 75 are positioned on the locking portions 79 of the clasp members 68, 69, 70 such that they are configured to align with each other to indicate proper alignment of the first clasp member 68 (or the third clasp member 70) and the second clasp member 69 to form the mating engagement, as will be discussed below. The smooth-textured protrusions 75 may be configured to visually stand out from the rough-textured surface 76 to provide a visual cue to the user that the clasp members 68, 69, 70 are properly aligned and positioned with respect to each other to form the mating engagement.

Figure 15:
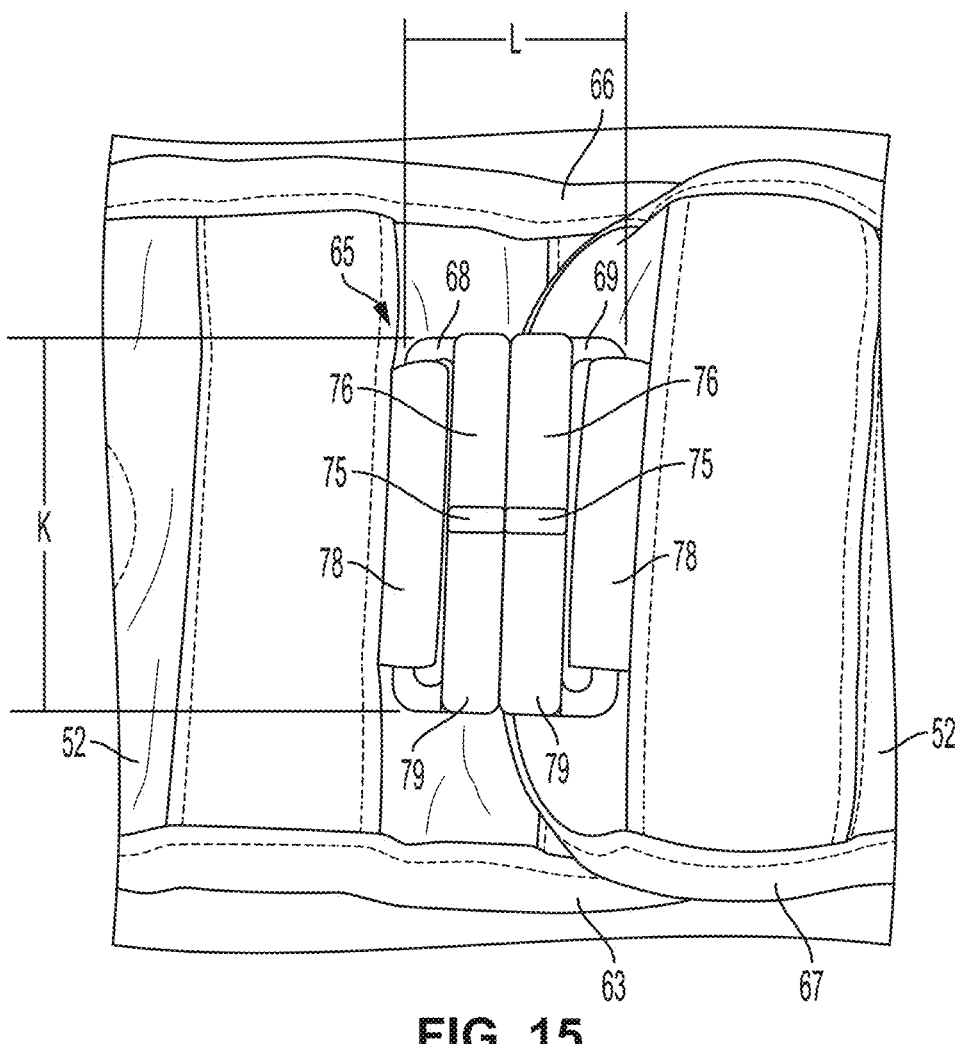
FIG. 15 is an enlarged view of a closure mechanism for connecting ends of a belt of the support garment of FIGS. 4A and 4B that may be used in connection with the present disclosure.
Figure 17A:
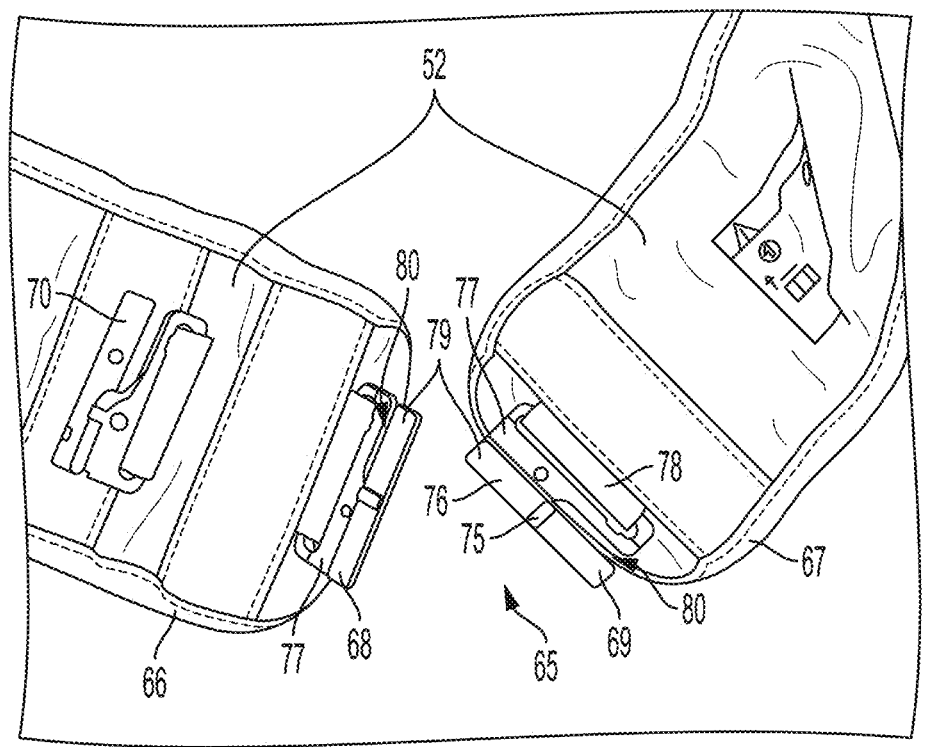
FIGS. 17A-17D are a sequence of views illustrating a process for matingly engaging the clasp members of the closure mechanism of FIG. 15.
Figure 17B:
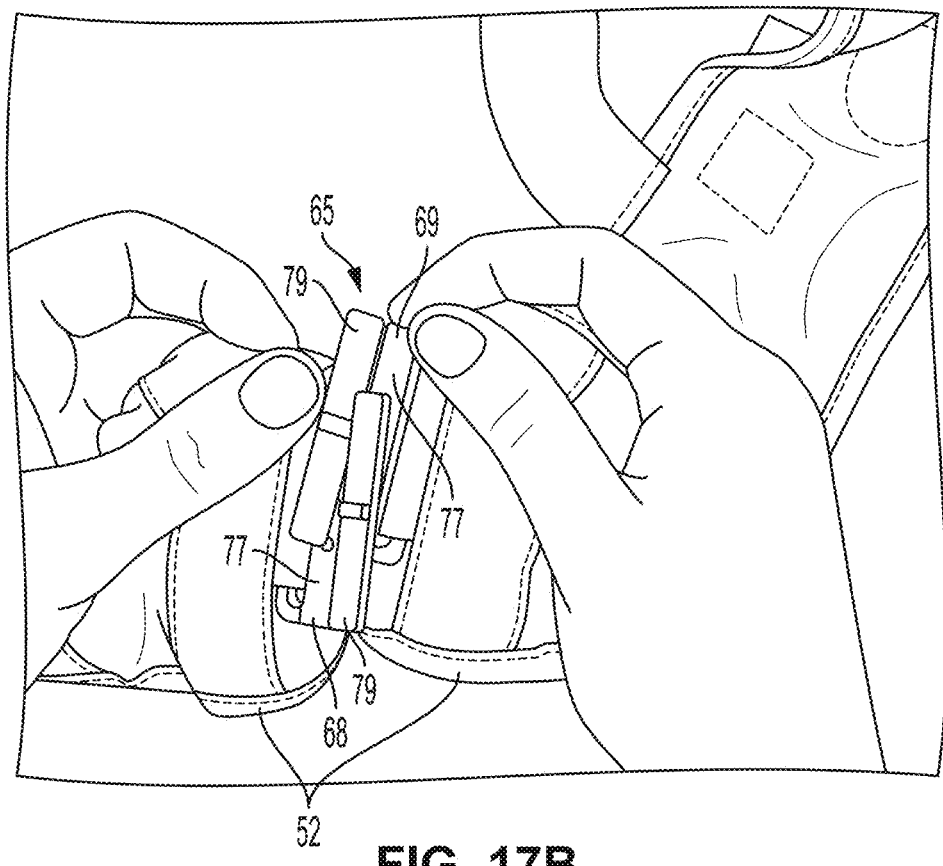
Figure 17C:
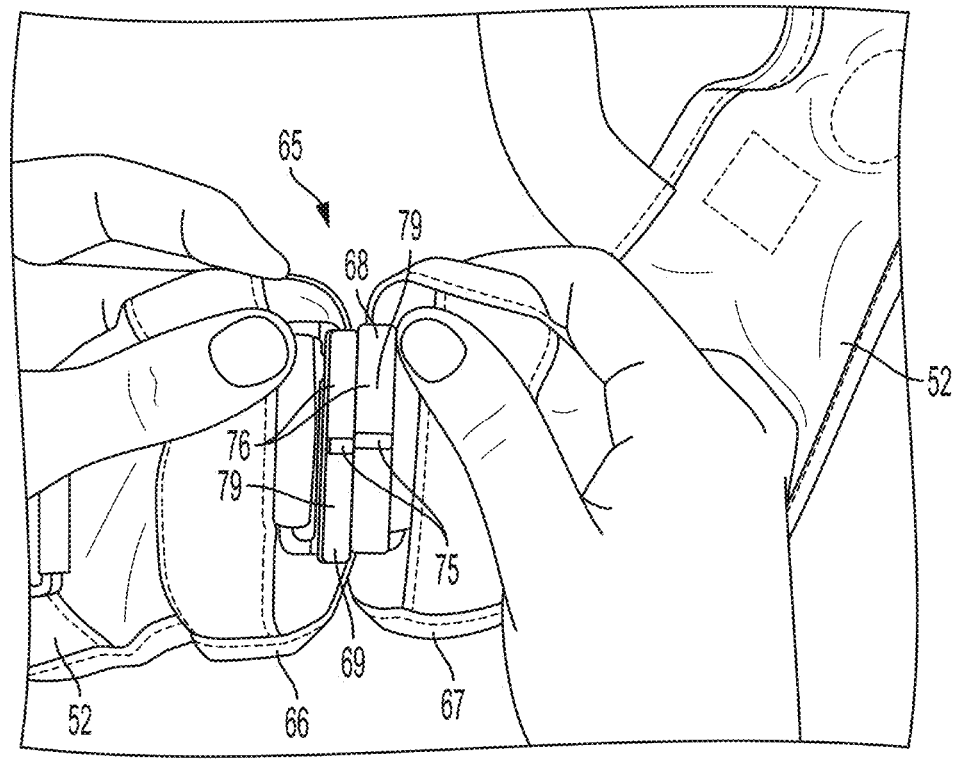
Figure 17D:
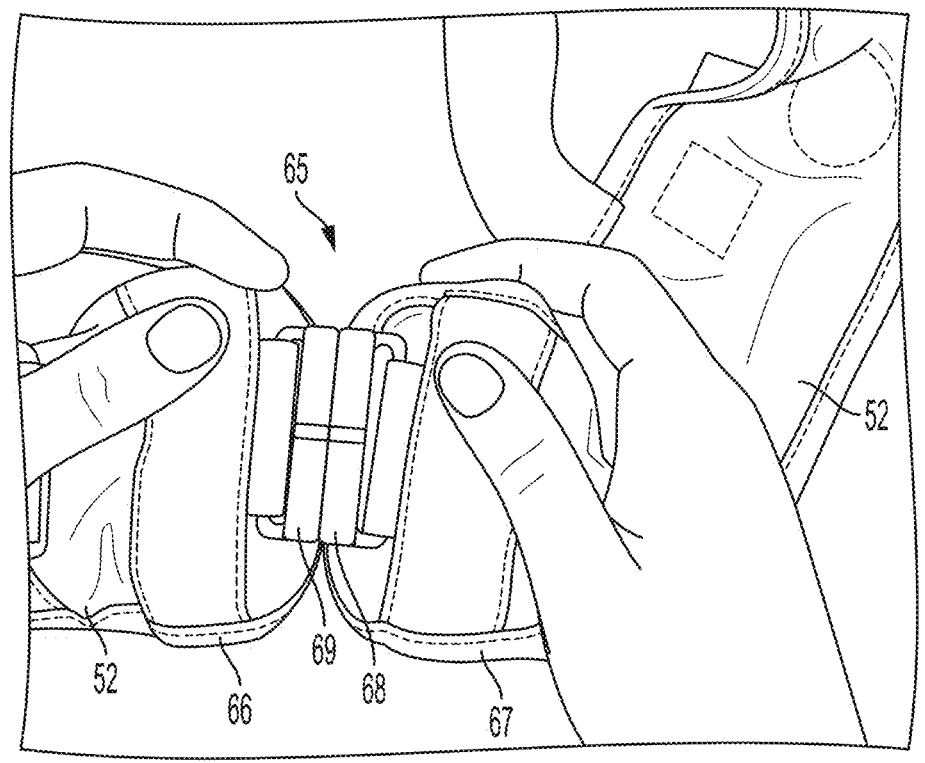

FIGS. 17A-17D illustrate an exemplary sequence for securing the first and second clasp members 68, 69 to form the mating engagement and thereby close the respective ends 66, 67 of the belt 52 to each other at the front of the patient. The open ends 66, 67 of the belt 52 are brought together until the open-ended slots 80 of the clasp members 68, 69 are aligned with each other to allow the clasp members 68, 69 to be slid or moved toward each other such that the closed end of the open-ended slot 81 of each clasp member 68, 69 becomes disposed in the open-ended slot 68 of the other clasp member 69, 68 (FIG. 17B). The clasp members 68, 69 are slid together until post 71 and hook 73 on the locking portion 79 of each clasp member 68, 69 are aligned with the hole 72 and notch 74, respectively, of the other clasp member 69, 98 and the clasp members 68, 69 are positioned to form the mating engagement (FIG. 17C). The smooth protrusions 75 on the locking portions 79 will align with each other when the clasp members 68, 69 are properly positioned to indicate to the user that the clasp members 68, 69 can be secured in the mating engagement. The clasp members 68, 69 can then be pivoted toward each other such that the post 71 and hook 73 on the locking portion 79 of each clasp member 68, 69 comes into engagement with the hole 72 and notch 74, respectively, on the other clasp member 69, 68 to physically align and lock the clasp members 68, 69 together in the mating engagement with the locking portions 79 covering the recessed portions 77 (FIGS. 15 and 17D). When the hooks 73 engage with the notches 74 and/or when the posts 71 engage with the holes 72, a tactile and/or audible click or snap is produced to provide tactile and/or audible feedback that the clasp members 68, 69 are properly secured in the mating engagement. The click or snap may also be produced when the clasp members 68, 69 are disengaged.

According to an example, the clasp members 68, 69, 70 each have a color complementary to a color of a fabric material F of the support garment 50. For instance, the color of the clasp members 68, 69, 70 may be PANTONE 18-4005 (Steel Gray), which is a suitable complement for the gray color of the support garment 50, as discussed above. It is to be appreciated that the clasp members 68, 69, 70 may be provided in any suitable color.

As shown in FIG. 15, according to an example, the closure mechanism 65, i.e., the first clasp member 68 and the second clasp member 69 when secured, has a height K of approximately 40 mm-50 mm, more particularly approximately 45 mm-47 mm, more particularly 45.75 mm. The closure mechanism 65 may have a width L of approximately 20 mm-35 mm when the first and second clasp members 68, 69 form the mating engagement, more particularly approximately 26 mm-28 mm, more particularly 27.2 mm. The closure mechanism 65 may have a maximum thickness of approximately 3 mm-8 mm, more particularly approximately 5 mm-6 mm, more particularly approximately 5.75 mm. It is to be appreciated that the closure mechanism 65 may be provided in any suitable size to facilitate handling of the closure mechanism 65 and opening and closing of the belt 52 of the support garment 50.

It is to be appreciated that the closure mechanism 65 may be of any type and configuration suitable for fastening the support garment 50 on the patient's body. For instance, the closure mechanism 65 may include any one of or combinations of the following mechanisms: corresponding hooks and eyes disposed on opposing ends 66, 67 of the belt 52; a zipper; corresponding hook-and-loop fasteners disposed on the belt 52; buttons; snaps; one or more tension hooks disposed on one side portion of the belt 52 engageable with fabric loops disposed on the other side portion; a mechanical locking clip; and corresponding rail and track members fastened to opposing side portions of the belt 52 by stretchable fabric that may be slid together with the rail member fitted within the track member.

Aspects of the present disclosure are directed to monitoring and/or therapeutic medical devices configured to identify a patient physiological event and, in response to the identified event, to provide a notification to the patient wearing the device. The notification can include an instruction or request to perform a patient response activity. Successful completion of the patient response activity can cause the device to suspend or delay a device function, such as administering a treatment to a patient and/or issuing an alert or alarm.

In some examples, the medical device includes monitoring circuitry configured to sense physiological information of a patient. The controller can be configured to detect the patient physiological event based, at least in part, on the sensed physiological information. A patient event can be a temporary physiological problem or abnormality, which can be representative of an underlying patient condition. A patient event can also include injuries and other non-recurring problems that are not representative of underlying physiological condition of the patient. A non-exhaustive list of patient events that can be detected by an external medical device includes, for example: bradycardia, ventricular tachycardia (VT) or ventricular fibrillation (VF), atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventricular arrhythmias such as premature ventricular contractions (PVCs) and accelerated idioventricular rhythm.

In some examples, the device controller is configured to notify the patient of the detection of the one or more events and to receive a patient response to the notification. The patient response can include performing a response activity identifiable by an input component associated with the medical device. In general, the response activity is selected to demonstrate or to provide information about the status of the patient and, in particular, to confirm that the patient is conscious and substantially aware of his or her surroundings. The response activity or activities can also be configured to confirm patient identity (e.g., that the person providing the response is the patient, rather than a bystander or impostor). The response activity can also demonstrate or test a patient ability such as one or more of psychomotor ability, cognitive awareness, and athletic/movement ability. In some examples, the response activity can be a relatively simple action, such as making a simple or reflexive movement in response to a stimulus applied by the device. In other examples, more complex activities, such as providing answers to questions requiring reasoning and logical analysis can be required. The device can be configured to select a particular response activity based on characteristics of the patient and/or the detected patient event.

In some examples, the device can instruct the patient to perform several actions that are each representative of patient ability. In other modes, the device can instruct the patient to perform different types of activities that are representative of different patient abilities. For example, the device can instruct the patient to perform a single activity requiring several patient abilities to complete correctly. Alternatively, the device can instruct the patient to perform a first activity representative of a first patient ability and, once the first activity is correctly completed, to perform a second activity representative of a second patient ability.

This disclosure relates to components, modules, subsystems, circuitry, and/or techniques for use in external medical devices. For example, such components, modules, subsystems, circuitry, and/or techniques can be used in the context of medical devices for providing treatment to and/or monitoring a patient. For example, such medical devices can include monitoring devices configured to monitor a patient to identify occurrence of certain patient events. In some implementations, such devices are capable, in addition to monitoring for patient conditions, of providing treatment to a patient based on detecting a predetermined patient condition.

In some examples, the medical device can be a patient monitoring device, which can be configured to monitor one or more of a patient's physiological parameters without an accompanying treatment component. For example, a patient monitor may include a cardiac monitor for monitoring a patient's cardiac information. Such cardiac information can include, without limitation, heart rate, ECG data, heart sounds data from an acoustic sensor, and other cardiac data. In addition to cardiac monitoring, the patient monitor may perform monitoring of other relevant patient parameters, including glucose levels, blood oxygen levels, lung fluids, lung sounds, and blood pressure.

FIGS. 19-21 illustrate an exemplary wearable medical device 100, such as a wearable defibrillator, which may incorporate the exemplary support garment 50 discussed above with reference to FIGS. 4A-18.

Non-limiting examples of suitable wearable defibrillators are disclosed in U.S. Pat. Nos. 4,928,690; 5,078,134; 5,741, 306; 5,944,669; 6,065,154; 6,253,099; 6,280,461; 6,681, 003; 8,271,082; and 8,369,944, the disclosure of each of which is hereby incorporated by reference. The wearable medical device 100 includes a plurality of sensing electrodes 112 that can be disposed at various positions about the patient's body. The sensing electrodes 112 are electrically coupled to a medical device controller 120 through a connection pod 130. In some implementations, some of the components of the wearable medical device 100 are affixed to a garment 110 that can be worn on the patient's torso. According to an example of the present disclosure, the garment 110 shown in FIG. 19 may be the same as the support garment 50 discussed above with reference to FIG. 4A-18.

The devices described herein are capable of continuous, substantially continuous, long-term and/or extended use or wear by, or attachment or connection to, a patient. In this regard, the device may be configured to be used or worn by, or attached or connected to, a patient, without substantial interruption, for example, up to hours or beyond (e.g., weeks, months, or even years). For example, in some implementations, such a period of use or wear may be at least 4 hours. For example, such a period of use or wear may be at least 24 hours or one day. For example, such a period of use or wear may be at least 7 days. For example, such a period of use or wear may be at least one month. In some implementations, such devices may be removed for a period of time before use, wear, attachment, or connection to the patient is resumed, e.g., to change batteries, to change or wash the garment, and/or to take a shower. Similarly, the device may be configured for continuous, substantially continuous, long-term and/or extended monitoring of one or more patient physiological conditions. For instance, in addition to cardiac monitoring, the medical device may be capable of monitoring a patient for other physiological conditions. Accordingly, in implementations, the device may be configured to monitor blood oxygen, temperature, glucose levels, sleep apnea, snoring and/or other sleep conditions, heart sounds, lung sounds, tissue fluids, etc. using a variety of sensors including radio frequency (RF) sensors, ultrasonic sensors, electrodes, etc. In some instances, the device may carry out its monitoring in periodic or aperiodic time intervals or times. For example, the monitoring during intervals or times can be triggered by a patient action or another event. For example, one or more durations between periodic or aperiodic intervals or times can be patient and/or other non-patient user configurable.

For example, as shown in FIG. 19, the controller 120 can be mounted on a belt worn by the patient 102. The sensing electrodes 112 and connection pod 130 can be assembled or integrated into the garment 110 as shown. The sensing electrodes 112 are configured to monitor the cardiac function of the patient 102 (e.g., by monitoring one or more cardiac signals of the patient 102). While FIG. 19 shows four sensing electrodes 112, additional sensing electrodes may be provided, and the plurality of sensing electrodes 112 may be disposed at various locations about the patient's body.

The wearable medical device 100 can also optionally include a plurality of therapy electrodes 114 that are electrically coupled to the medical device controller 120 through the connection pod 130. The therapy electrodes 114 are configured to deliver one or more therapeutic transcutaneous defibrillating shocks, transcutaneous pacing pulses, and/or TENS pulses to the body of the patient 102 if it is determined that such treatment is warranted. The connection pod 130 may include electronic circuitry and one or more sensors (e.g., a motion sensor, an accelerometer, etc.) that are configured to monitor patient activity. In some implementations, the wearable medical device 100 may be a monitoring-only device that omits the therapy delivery capabilities and associated components (e.g., the therapy electrodes 114). In some implementations, various treatment components may be packaged into various modules that can be attached or removed from the wearable medical device 100 as needed. As shown in FIG. 19, the wearable medical device 100 may include a patient interface pod 140 that is electrically coupled to, integrated in, and/or integrated with the patient interface of the medical device controller 120. For example, the patient interface pod 140 may include patient interface elements such as a speaker, a microphone responsive to patient input, a display, an interactive touch screen responsive to patient input, and/or physical buttons for input.

Figure 20B:
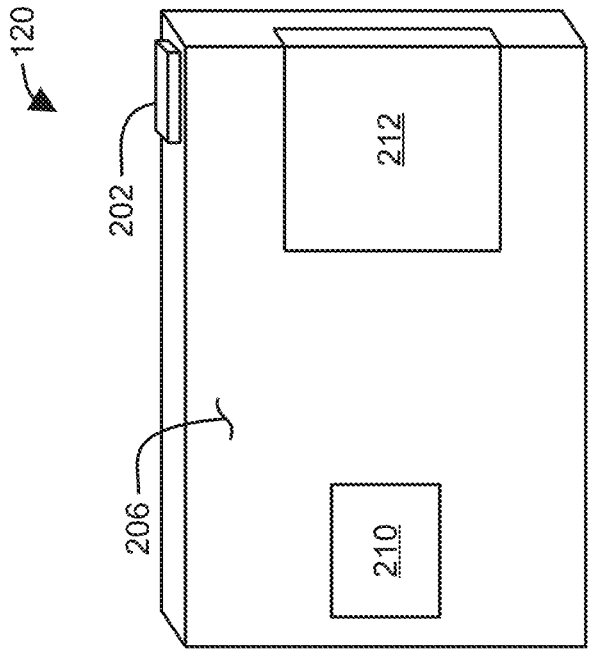
FIG. 20B is a schematic drawing showing a rear perspective view of the example monitor of FIG. 20B.
Figure 20A:
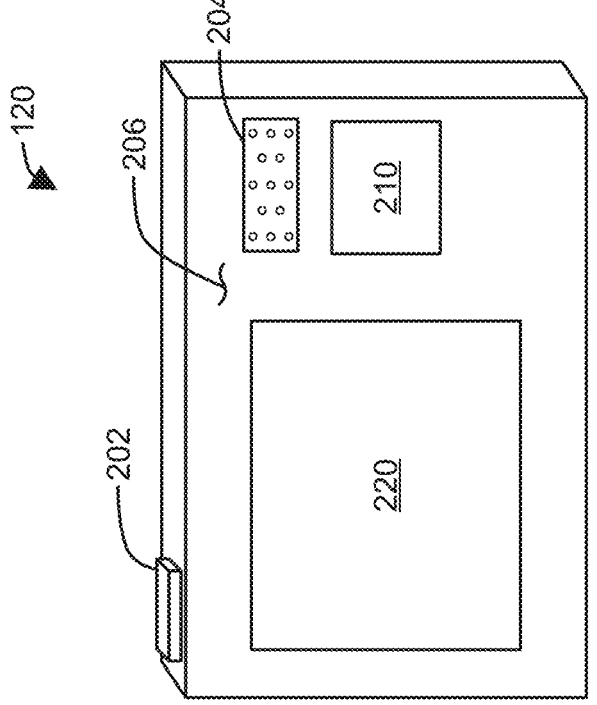
FIG. 20A is a schematic drawing showing a front perspective view of an example monitor for the wearable medical device of FIG. 19.
Figure 21:
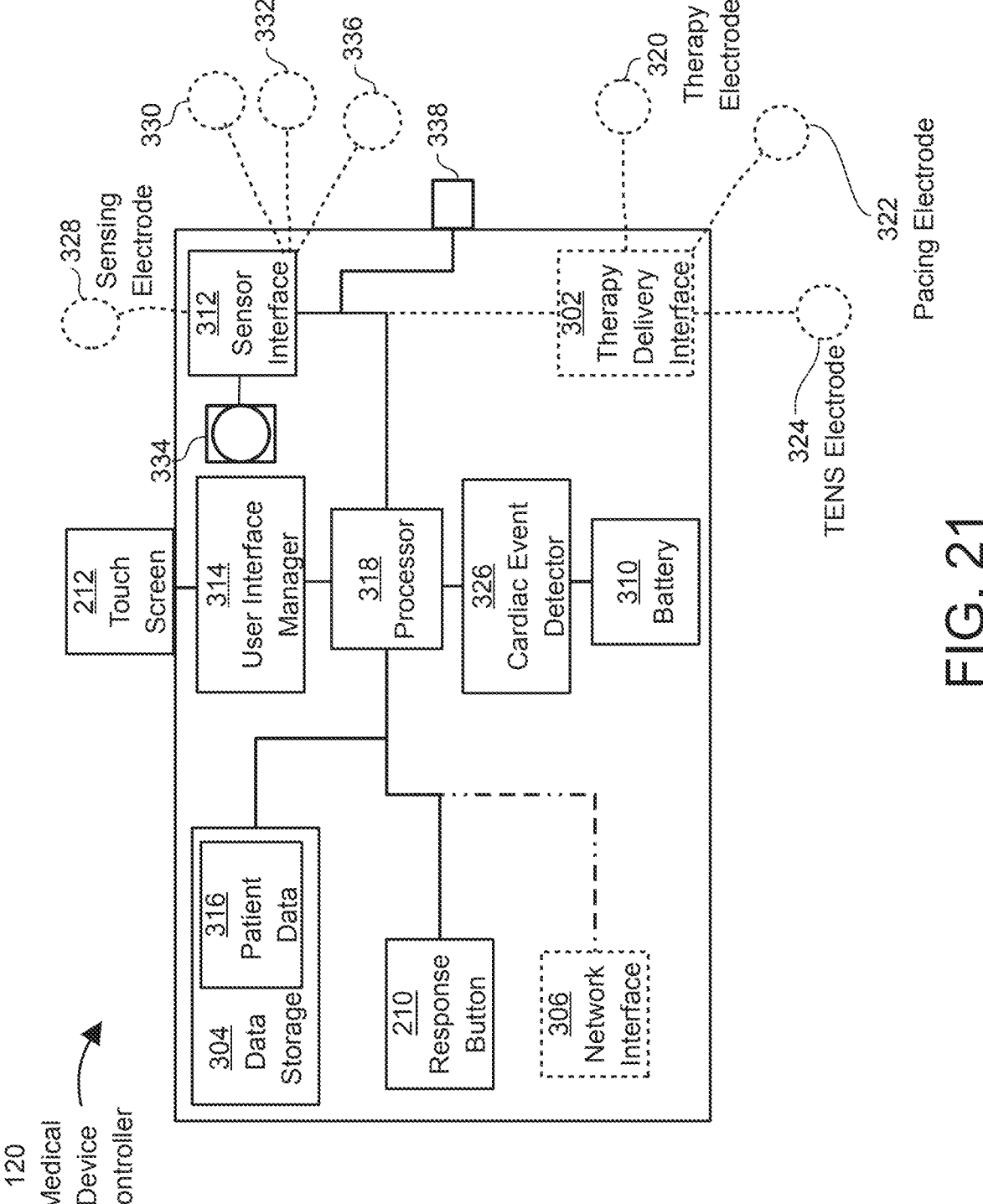
FIG. 21 is a schematic diagram of functional components of the wearable medical device of FIG. 19.

With reference to FIGS. 20A and 20B, an example of the medical device controller 120 is illustrated. The controller 120 may be powered by a rechargeable battery 212. The rechargeable battery 212 may be removable from a housing 206 of the medical device controller 120 to enable a patient and/or caregiver to swap a depleted (or near-depleted) battery 212 for a charged battery. The controller 120 includes a patient interface such as a touch screen 220 that can provide information to the patient, caregiver, and/or bystanders. In some implementations, in addition to or instead of a touch screen 220, the controller 120 may interact with the patient (e.g., receive patient input or provide information to the patient as described herein) via patient interface pod 140 (shown in FIG. 19). The patient interface pod 140 may be operatively coupled to the controller 120. In an example, the controller 120 may be configured to detect that if the patient interface pod 140 is operatively coupled to the controller 120, the controller 120 may then disable the patient interface elements of the controller 120 (e.g., touch screen 220) and instead communicate via the patient interface pod 140. The patient interface pod 140 may be wirelessly coupled with the controller 120. The patient interface pod 140 may take other forms and include additional functionality. For instance, the patient interface pod 140 may be implemented on a smartphone, tablet, or other mobile device carried by the patient. In another example, the patient interface pod 140 may be worn as a watch about the wrist of the patient, or as a band about an upper arm of the patient. In some implementations, the controller 120 may communicate certain alerts and information and/or be responsive to patient input via both the patient interface elements included in the controller 120 and the patient interface pod 140. The patient and/or caregiver can interact with the touch screen 220 or the patient interface pod 140 to control the medical device 100. The controller 120 also includes a speaker 204 for communicating information to the patient, caregiver, and/or the bystander. The controller 120 (and/or the patient interface pod 140) may include one or more response buttons 210. In some examples, when the controller 120 determines that the patient is experiencing cardiac arrhythmia, the speaker 204 can issue an audible alarm to alert the patient and bystanders to the patient's medical condition. In some examples, the controller 120 can instruct the patient to press one or both of the response buttons 210 to indicate that he or she is conscious, thereby instructing the medical device controller 120 to withhold the delivery of therapeutic defibrillating shocks. If the patient does not respond to an instruction from the controller 120, the medical device 100 may determine that the patient is unconscious and proceed with the treatment sequence, culminating in the delivery of one or more defibrillating shocks to the body of the patient. In some examples, as discussed in further detail herein, the controller 120 can additionally or alternatively instruct the patient to perform a response activity to indicate that he or she is conscious and further provide information to the controller 120 regarding the patient's status. For example, the controller 120 can instruct the patient to touch or manipulate the touch screen 220 or an interactive display on the patient interface pod 140 in a coordinated manner to confirm that he or she is conscious and has requisite awareness and/or psychomotor ability. In this way, the patient response confirms not only that buttons 210 were pressed, but that the patient is sufficiently conscious and aware to perform a response activity as instructed. The medical device controller 120 may further include a port 202 to removably connect sensing devices (e.g., ECG sensing electrodes 112) and/or therapeutic devices (e.g., therapy electrodes 114 shown in FIG. 19) to the medical device controller 120.

With reference to FIG. 21, a schematic example of the medical device controller 120 of FIGS. 19, 20A, and 20B is illustrated. As shown in FIG. 21, the controller 120 includes at least one processor 318, a patient interface manager 314, a sensor interface 312, an optional therapy delivery interface 302, data storage 304 (which may include patient data storage 316), an optional network interface 306, a patient interface 308 (e.g., including the touch screen 220 shown in FIGS. 20A and 20B), and a battery 310. The sensor interface 312 can be coupled to any one or combination of sensors to receive information indicative of cardiac activity. For example, the sensor interface 312 can be coupled to one or more sensing devices including, for example, sensing electrodes 328, contact sensors 330, pressure sensors 332, accelerometers or motion sensors 334, and radio frequency (RF)-energy based sensors 331 (e.g., tissue fluid sensors). The controller 120 can also include an optical sensor 336, such as a digital camera, for capturing static or video images of the device surroundings. Although designs from different vendors are different, a digital camera usually consists of a charge-coupled device (CCD) or complementary metal-oxide-semiconductor (CMOS) imaging sensor, a lens, a multifunctional video control chip, and a set of discrete components (e.g., capacitor, resistors, and connectors). The therapy delivery interface 302 (if included) can be coupled to one or more electrodes that provide therapy to the patient including, for example, one or more therapy electrodes 320, pacing electrodes 322, and/or TENS electrodes 324. The sensor interface 312 and the therapy delivery interface 302 may implement a variety of coupling and communication techniques for facilitating the exchange of data between the sensors and/or therapy delivery devices and the controller 120.

The medical device controller 120 may comprise one or more input components configured to receive a response input from the patient. The input components may comprise at least one of: the response button 210; the touch screen 220; an audio detection device, such as a microphone 338; the motion sensor 334; the contact sensor 330; the pressure sensor 332; a gesture recognitions component, such as the optical sensor 336; or a patient physiological sensor, such as the sensing electrodes 328.

In some examples, the medical device controller 120 includes a cardiac event detector 326 to monitor the cardiac activity of the patient and identify cardiac events experienced by the patient based on received cardiac signals. In other examples, cardiac event detection can be performed using algorithms for analyzing patient ECG signals obtained from the sensing electrodes 328. Additionally, the cardiac event detector 326 can access patient templates (e.g., which may be stored in the data storage 304 as patient data 316) that can assist the cardiac event detector 326 in identifying cardiac events experienced by the particular patient (e.g., by performing template matching algorithms).

The at least one processor 318 can perform a series of instructions that control the operation of the other components of the controller 120. In some examples, the patient interface manager 314 is implemented as a software component that is stored in the data storage 304 and executed by the at least one processor 318 to control, for example, the patient interface component 308. The patient interface manager 314 can control various output components and/or devices of the medical device controller 120 (e.g., patient interface 220 and/or patient interface pod 140 shown in FIG. 19) to communicate with external entities consistent with various acts and/or display screens described herein. For example, such output components and/or devices can include speakers, tactile and/or vibration output elements, visual indicators, monitors, displays, LCD screens, LEDs, Braille output elements, and the like. Additionally, the patient interface manager 314 can be integrated with the treatment-providing components of the controller 120 so that the patient can control and, in some cases, suspend, delay, or cancel treatment using the patient interface.

Although a wearable medical device and a support garment for such a device have been described in detail for the purpose of illustration based on what is currently considered to be the most practical examples, it is to be understood that such detail is solely for that purpose and that the subject matter of this disclosure is not limited to the disclosed examples, but, on the contrary, is intended to cover modifications and equivalent arrangements. For example, it is to be understood that this disclosure contemplates that, to the extent possible, one or more features of any example can be combined with one or more features of any other example.

The invention claimed is:

1. A wearable cardiac therapeutic device for easy and quick donning and removal about a torso of a patient, comprising:

a plurality of ECG sensing electrodes configured to sense ECG signals regarding a cardiac function of the patient;

a plurality of therapy electrodes to deliver transcutaneous defibrillation shocks or transcutaneous pacing pulses to the patient's heart in an event of a life-threatening cardiac arrhythmia; and a support garment configured to support and hold the plurality of ECG sensing electrodes and the plurality of therapy electrodes against the patient's body, the support garment comprising:

a back portion;

a belt defined by side portions extending from the back portion and around a front of the patient's torso configured to support one or more of the plurality of ECG sensing electrodes against skin of the patient at a proper position; and a closure mechanism configured to connect the side portions at the front of the patient's torso in a manner to facilitate the support garment to support and hold the plurality of ECG sensing electrodes while the plurality of ECG sensing electrodes senses the ECG signals regarding the cardiac function of the patient and while the plurality of therapy electrodes delivers the transcutaneous defibrillation shocks or transcutaneous pacing pulses to the patient's heart, the closure mechanism comprising:

a first clasp member disposed on one of the side portions; and a second clasp member disposed on another of the side portions, the second clasp member comprising a member that is an identical shape as the first clasp member, wherein the first and second clasp members are configured to form a mating engagement with each other to secure the side portions with the plurality of ECG sensing electrodes secured and in contact with the skin of the patient at the proper position upon complete mating engagement between the first and second clasp members of the closure mechanism, and wherein the first and second clasp members are configured to facilitate mutual alignment and securing of the side portions at the front of the patient, provide tactile feedback to a user that the clasp members are matingly engaged and thereby indicate to the patient that the cardiac therapeutic device has been correctly donned to protect the patient from life-threatening cardiac arrhythmia events.

2. The wearable cardiac therapeutic device according to claim 1, wherein at least one of the first and second clasp members is connected to the respective side portion by a belt attachment and an adjustable slider.

3. The wearable cardiac therapeutic device according to claim 1, further comprising a third clasp member disposed on the same side portion as the first clasp member at a different location along a length of the side portion, the third clasp member comprising a member that is an identical shape as the first clasp member and the second clasp member and being configured to form a mating with the second clasp member to secure the side portions.

4. The wearable cardiac therapeutic device according to claim 1, wherein the first clasp member comprises first protrusion and recess features and the second clasp member comprises corresponding second protrusion and recess features, wherein at least one of the first protrusion and recess features or the second protrusion and recess features are configured to indicate proper alignment of the clasp members, to form the mating engagement between the clasp members, and to engage each other to secure the clasp members in the mating engagement, and wherein the first and second protrusion and recess features are also configured to snap together to provide tactile feedback to the user.

5. The wearable cardiac therapeutic device according to claim 1, wherein the first clasp member and the second clasp member each comprises at least one smooth-textured protrusion disposed on a rough-textured exterior surface, the smooth-textured protrusions being configured to align with each other to indicate proper alignment of the clasp members to form the mating engagement.

6. The wearable cardiac therapeutic device according to claim 1, wherein the support garment comprises a gray color fabric material, and wherein the first clasp member and the second clasp member each have a color complementary to the gray color fabric material of the support garment.

7. The wearable cardiac therapeutic device according to claim 1, wherein the closure mechanism has a height of approximately 40 mm-50 mm, a width of approximately 20 mm-35 mm when the first and second clasp members form the mating engagement, and a maximum thickness of approximately 3 mm-8 mm.

8. The wearable cardiac therapeutic device according to claim 1, further comprising a medical device controller in communication with the plurality of ECG sensing electrodes and the plurality of therapy electrodes, the medical device controller configured to:

detect a patient event based, at least in part, on the ECG signals sensed by the plurality of ECG sensing electrodes; and provide a therapy to the patient via the plurality of therapy electrodes in response to a detection of the patient event, wherein the patient event detected by the medical device controller comprises one or more of bradycardia, ventricular tachycardia or ventricular fibrillation, atrial arrhythmias such as premature atrial contractions, multifocal atrial tachycardia, atrial flutter, and atrial fibrillation, supraventricular tachycardia, junctional arrhythmias, tachycardia, junctional rhythm, junctional tachycardia, premature junctional contraction, and ventricular arrhythmias such as premature ventricular contractions and accelerated idioventricular rhythm.

9. The wearable cardiac therapeutic device according to claim 8, wherein the medical device controller is configured to issue an audible alarm to notify the patient that the patient event has been detected.

10. The wearable cardiac therapeutic device according to claim 8, wherein the medical device controller comprises one or more input components configured to receive a response input from the patient, wherein the one or more input components comprise at least one of: a response button; a touch screen; an audio detection device; a motion sensor; a contact sensor; a pressure sensor; a gesture recognition component; or a patient physiological sensor.

11. The wearable cardiac therapeutic device according to claim 1, wherein the support garment comprises a plurality of circular hook-and-loop fastener patches on an inside surface thereof for fastening and supporting the plurality of ECG sensing electrodes on the support garment, wherein each of the plurality of ECG sensing electrodes comprises a corresponding hook-and-loop fastener configured to connect to a respective circular hook-and-loop fastener patch on the support garment, and wherein the plurality of circular hook-and-loop fastener patches are configured to facilitate alignment and assembly of the respective ECG sensing electrodes on the support garment and provide for fastening and support for the respective ECG sensing electrodes on the support garment independent of a rotational orientation of the respective ECG sensing electrodes.

12. The wearable cardiac therapeutic device according to claim 11, wherein the plurality of circular hook-and-loop fastener patches and the corresponding hook-and-loop fasteners are color coded to facilitate assembly of each of the plurality of ECG sensing electrodes to a corresponding predetermined location on the inside surface of the support garment.

13. The wearable cardiac therapeutic device according to claim 1, wherein the support garment further comprises:

a plurality of support pockets disposed on an inside surface of the support garment for supporting the plurality of therapy electrodes on the support garment; and a plurality of handling tab members, at least one handling tab member being fastened to each of the plurality of support pockets, the plurality of handling tab members being configured to facilitate opening and closing of the plurality of support pockets for assembly of the plurality of therapy electrodes therein, wherein each of the handling tab members comprises a fabric tape formed in a loop extending from an outer surface of a respective one of the plurality of support pockets to an inner surface of the respective support pocket, and wherein each of the handling tab members has a length and width configured to facilitate physical manipulation of the handling tab member by at least one of: grasping the handling tab member or inserting a finger into the loop.

14. The wearable cardiac therapeutic device according to claim 13, wherein each of the plurality of handling tab members is color coded to correspond to a colored indicator provided on a respective therapy electrode.

15. The wearable cardiac therapeutic device according to claim 13, wherein each of the plurality of handling tab members comprises a female or male plastic snap member disposed thereon configured to form a mating engagement with a counterpart male or female plastic snap member disposed on the inside surface of the support garment for releasably securing the respective support pocket in a closed condition, wherein the female or male plastic snap member is configured to provide tactile feedback when the female or male plastic snap member disposed on the handling tab member is secured to the female or male plastic snap member disposed on the inside surface of the support garment.

16. The wearable cardiac therapeutic device according to claim 15, further comprising a distribution box, wherein the support garment further comprises at least one flap for securing the distribution box on the support garment and at least one plastic snap is disposed on the at least one flap and the inside surface of the support garment for releasably securing the flap in a position securing the distribution box, wherein each of the at least one flap comprises a female or male plastic snap member disposed thereon configured to form a mating engagement with a counterpart male or female plastic snap member disposed on the inside surface of the support garment for releasably securing the respective flap, and wherein an arrangement of the female and male plastic snap members for releasably securing the at least one support pocket is reversed from an arrangement of the female and male plastic snap members for releasably securing the at least one flap.

17. The wearable cardiac therapeutic device according to claim 1, wherein the back portion and the side portions defining the belt are secured by a seam formed by aesthetic flatlock stitching.

18. The wearable cardiac therapeutic device according to claim 1, wherein the support garment comprises a fabric having an anti-microbial treatment applied thereto, the anti-microbial treatment configured to limit or prevent odor and bacterial growth on the support garment.

19. The wearable cardiac therapeutic device according to claim 1, wherein the support garment comprises an aesthetic edge binding surrounding at least a portion of a periphery of the support garment, the aesthetic edge binding comprising nylon and spandex materials.

20. The wearable cardiac therapeutic device according to claim 1, wherein the support garment comprises:

at least one shoulder strap extending between the back portion and the belt, the at least one shoulder strap comprising a double plush elastic material;

at least one first strap slide configured to attach the at least one shoulder strap to the back portion; and at least one second strap slide configured to provide length adjustment to the at least one shoulder strap, wherein the at least one first strap slide and the at least one second strap slide each comprise a coated metal material and are configured to have a low profile, provide high coverage of the at least one shoulder strap and a comfortable feel to the patient, and facilitate physical manipulation and length adjustment of the at least one shoulder strap.

* * * * *